(12) United States Patent
Huang et al.

(10) Patent No.: US 8,669,244 B2
(45) Date of Patent: Mar. 11, 2014

(54) CUCURBITANE-TRITERPENOID COMPOUNDS, PHARMACEUTICAL COMPOSITION, USE AND PREPARATION METHOD THEREOF

(75) Inventors: Ching-Jang Huang, Taipei (TW); Yueh-Hsiung Kuo, Taipei (TW); Chin Hsu, Taipei (TW)

(73) Assignee: National Taiwan University, Taipei (TW)

( * ) Notice: Subject to any disclaimer, the term of this patent is extended or adjusted under 35 U.S.C. 154(b) by 271 days.

(21) Appl. No.: 13/173,200

(22) Filed: Jun. 30, 2011

(65) Prior Publication Data
US 2012/0252772 A1  Oct. 4, 2012

(30) Foreign Application Priority Data

Apr. 1, 2011  (TW) .............................. 100111592 A

(51) Int. Cl.
*A61K 31/585*  (2006.01)
*A61K 31/56*  (2006.01)
*C07J 71/00*  (2006.01)
*C07J 9/00*  (2006.01)

(52) U.S. Cl.
USPC ............... 514/175; 514/182; 540/73; 540/90; 552/544

(58) Field of Classification Search
USPC ................ 514/175, 182; 540/73, 90; 552/544
See application file for complete search history.

(56) References Cited

PUBLICATIONS

Ramalhete et al., "Cucurbitane-Type Triterpenoids from the African Plant *Momordica balsamina*". J. Nat. Prod., vol. 72, pp. 2009-2013, 2009.*

* cited by examiner

Primary Examiner — Barbara P Badio
(74) Attorney, Agent, or Firm — WPAT, P.C.; Anthony King

(57) ABSTRACT

Disclosed is a cucurbitane-triterpenoid compound for activating estrogen receptor activity, and a pharmaceutical composition, use and preparation method thereof. The cucurbitane-triterpenoid compound is presented as formula (I):

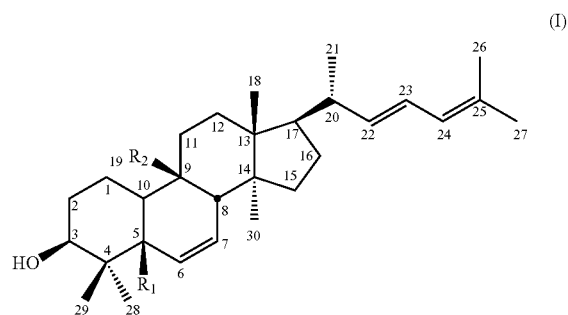

wherein a single bond or a double bond is formed between C5 and C10, and a single bond or a double bond is fromed between C8 and C9; when a single bond is formed between C5 and C10, the $R_1$ is oxygen; while a single bond is formed between C8 and C9, $R_2$ is carbonyl group (—C═O), methyl hydroxyl group (—CH(OH)), methyl ketone or methyl dimethoxy group (—CH(OCH$_3$)$_2$); and wherein while $R_1$ is oxygen (—O—) and $R_2$ is carbonyl group (—C═O) or methyl hydroxyl group (—CH(OH)), a single bond is formed between $R_1$ (—O—) and C19 of $R_2$ such that $R_1$ and $R_2$ are formed tetrahydro-2H-pyran-2-one or hemiacetal ring.

11 Claims, 33 Drawing Sheets

(C)

FTIR of Compound 1

FTIR of Compound 2

(D)

HRMS of Compound 3

FTIR of Compound 3

FTIR of Compound 4

FTIR of Compound 5

CUCURBITANE-TRITERPENOID COMPOUNDS, PHARMACEUTICAL COMPOSITION, USE AND PREPARATION METHOD THEREOF

FIELD OF THE INVENTION

The present invention is related to a bioactive compound isolated from *Momordica charantia*, especially relating to cucurbitane-triterpenoid compounds, pharmaceutical composition, use and preparation method thereof.

BACKGROUND OF THE INVENTION

Female menstrual cycle is closely related to concentration change of two key hormones, the estrogen and progesterone. Normally at age 45 to 55, secretion of estrogen decreases significantly and consequently resulting progesterone decrease as well. Decrease of these female hormone levels may associate with menopause symptoms, such as hot flash, sweats, rapid heart beat, insomnia, nervousness, depression, vagina dryness, increased bone loss (easily bone fracture), cardiovascular diseases such as stroke, high blood pressure, and so on.

Since the 70's "hormone replacement therapy" (HRT) has been broadly used to relieve menopause symptoms described above. However, an increased association of estrogen-only HRT with breast cancer, ovarian cancer, cervical cancer, and endometrium cancer was revealed in previous reports, especially among those with inherent gene from a family or those already suffering from these cancers. It has been known that long term administration of estrogen may japrodize health and cause side effects, however, other alternative therapies also have side effects. Therefore, there is an unmet, urgent need for development of an estrogen active therapeutics or dietary supplements without side effect for menopause women to improve the symptoms. The material used in the present invention is a common food and traditional Chinese medicine, *Momordica charantia*, wherein estrogenic compounds can effectively activate estrogen receptor, ERα and ERβ. Furthermore, the compounds of the present invention can be applied and used as a pharmaceutical composition or dietary supplement compositions for improving the estrogen-deficiency related syndromes.

SUMMARY OF THE INVENTION

However, previous studies of *Momordica charantia* mainly focus on its biological functions regarding lowering blood sugar, blood lipid, anti-oxidation and immune regulation. The present invention discovers that non-saponifiable fraction ingredients of *Momordica charantia* exhibit significant activation of estrogen receptor (ER).

Therefore, one aspect of the present invention is to provide a cucurbitane-triterpenoid compound having the formula (I):

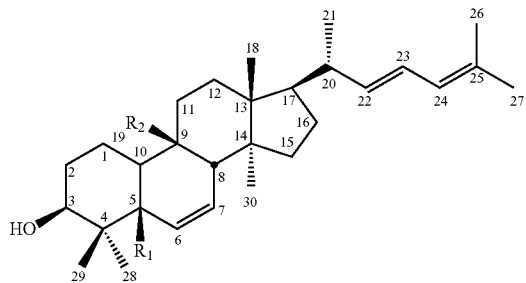

(I)

wherein a single bond or a double bond is formed between C5 and C10, and a single bond or a double bond is fromed between C8 and C9; when a single bond is formed between C5 and C10, the $R_1$ is oxygen; while a single bond is formed between C8 and C9, $R_2$ is carbonyl group (—C=O), methyl hydroxyl group (—CH(OH)), methyl ketone or methyl dimethoxy group (—CH(OCH$_3$)$_2$); and wherein while $R_1$ is oxygen (—O—) and $R_2$ is carbonyl group (—C=O) or methyl hydroxyl group (—CH(OH)), a single bond is formed between $R_1$ (—O—) and C19 of $R_2$ such that $R_1$ and $R_2$ are formed tetrahydro-2H-pyran-2-one or hemiacetal ring.

Preferably, the above compound is cucurbita-6,22(E),24-trien-3β-ol-19,5β-olide as shown as compound 1, 5β,19-epoxycucurbita-6,22(E),24-trien-3β,19-diol as shown as compound 2, 3β-hydroxycucurbita-5(10),6,22(E),24-tetraen-19-al as shown as compound 3, 19-dimethoxycucurbita-5(10),6,22(E),24-tetraen-3β-ol as shown as compound 4, or 19-nor-cucurbita-5(10),6,8,22(E),24-pentaen-3β-ol as shown as compound 5:

(compound 1)

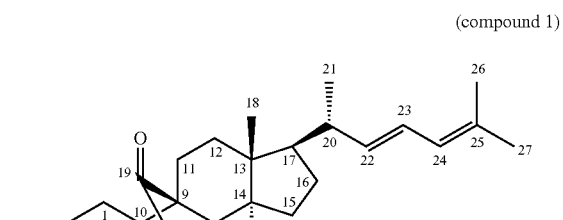

(compound 2)

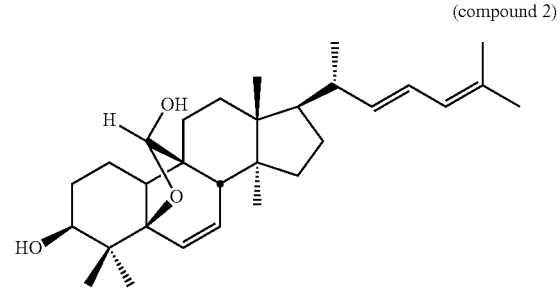

(compound 3)

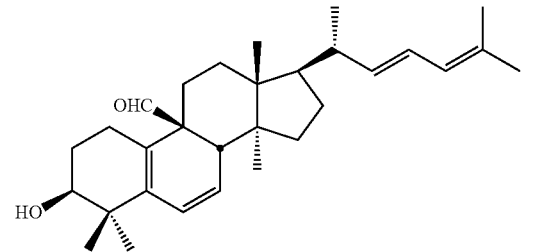

(compound 4)

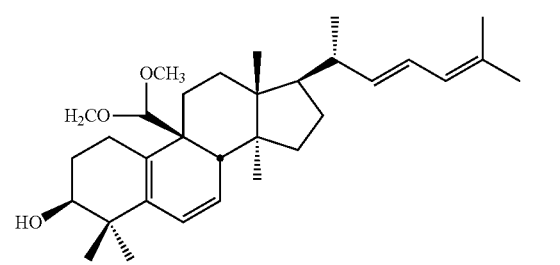

-continued (compound 5)

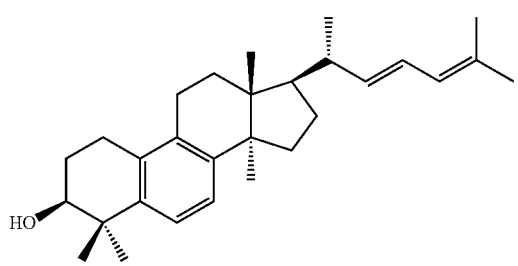

Another aspect of the present invention is to provide a method for regulation of estrogen receptor activity, comprising administering a cucurbitane-triterpenoid compound of group 1 or group 2 to a subject, wherein the group 1 is consisted of cucurbita-6,22(E),24-trien-3β-ol-19,5β-olide (compound 1), 5β,19-epoxycucurbita-6,22(E),24-trien-3β, 19-diol (compound 2), 19-nor-cucurbita-5(10),6,8,22(E),24-pentaen-3β-ol (compound 5) and 5β,19-epoxycucurtita-6, 24-diene-3β,23ξ-diol (compound 6); and
the group 2 is consisted of cucurbita-6,22(E),24-trien-3β-ol-19,5β-olide (compound 1), 5β,19-epoxycucurbita-6,22(E), 24-trien-3β,19-diol (compound 2), 3β-hydroxycucurbita-5 (10),6,22(E),24-tetraen-19-al (compound 3), 19-nor-cucurbita-5(10),6,8,22(E),24-pentaen-3β-ol (compound 5) and 5β,19-epoxycucurtita-6,24-diene-3β,23ξ-diol (compound 6); and when the cucurbitane-triterpenoid compound of the group 1 activates an estrogen receptor activity independently, whereas the cucurbitane-triterpenoid compound of the group 2 partly inhibits the estrogen receptor activity induced by endogenous estrogen; wherein compound 6 as shown in the following formula:

(compound 6)

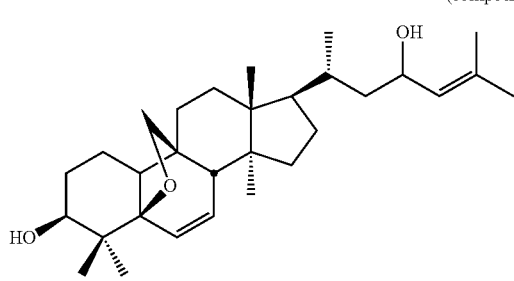

Another aspect of the present invention is to provide a pharmaceutical composition for regulation of estrogen receptor activity, comprising a group 1 or a group 2, wherein the group 1 is consisted of cucurbita-6,22(E),24-trien-3β-ol-19, 5β-olide (compound 1), 5β,19-epoxycucurbita-6,22(E),24-trien-3β,19-diol (compound 2), 19-nor-cucurbita-5(10),6,8, 22(E),24-pentaen-3β-ol (compound 5) and 5β,19-epoxycucurtita-6,24-diene-3β,23ξ-diol (compound 6); and the group 2 is consisted of cucurbita-6,22(E),24-trien-3β-ol-19,5β-olide (compound 1), 5β,19-epoxycucurbita-6,22(E), 24-trien-3β,19-diol (compound 2), 3β-hydroxycucurbita-5 (10),6,22(E),24-tetraen-19-al (compound 3), 19-nor-cucurbita-5(10),6,8,22(E),24-pentaen-3β-ol (compound 5), 5β,19-epoxycucurtita-6,24-diene-3β,23ξ-diol (compound 6), combinations or pharmaceutically acceptable salts thereof; and a diluent, an excipient or a carrier.

Another aspect of the present invention is to provide a method for preparing the cucurbitane-triterpenoid compound as described above from *Momordica charantia*, comprising steps of:
(a) extracting a pre-determined weight of *Momordica charantia* freeze dry powder with ethyl acetate (EA) at room temperature, evaporating by reduced pressure to remove ethyl acetate and obtaining an ethyl acetate extract and a residue;
(b) extracting the residue with ethanol (EtOH) at room temperature, evaporating by reduced pressure to remove ethanol and obtaining an ethanol extract;
(c) separating the ethanol extract with reverse phase column chromatography having coarse particle to obtain fraction 1, acid hydrolyzing the fraction 1 and extracting with ethyl acetate at room temperature, evaporating by reduced pressure to remove solvents and obtaining an acid hydrolysate;
(d) separating the acid hydrolysate with reverse phase column chromatography to obtain fraction 2; and
(e) purifying the fraction 2 of step (d) by using reverse phase and normal phase preparative HPLC to obtain the cucurbitane-triterpenoid compound with estrogenic activity.

The method of the present invention uses ethyl acetate and ethanol to extract *Momordica charantia* freeze dry powder then followed by further alkaline hydrolysis and acid hydrolysis treatment to obtain a fraction comprising novel phytoestrogen compounds those can activate transactivation of ER effectively and showed antagonistic activity toward estrogen induced ER activation. In the future, the present invention can be applied in improvement of women's menopause symptoms or patients with estrogen deficiency diseases. Not only do these compounds activate estrogen receptor to treat or improve these syndromes, they can be co-administered with estrogen therapeutics to selectively activate estrogen receptor. Thus these compounds have great potential to be developed as therapeutics or dietary supplements to relieve menopause symptoms or estrogen deficiency diseases. Furthermore, the cucurbitane-triterpenoid compounds of the present invention can partially inhibit the estrogen receptor activity induced by endogenous estrogen. For example, these compounds can inhibit endogenous estrogen activation and alleviate cancer proliferation in estrogen dependent breast cancer patients.

DETAILED DESCRIPTION OF THE PREFERRED EMBODIMENT

Figure 1:
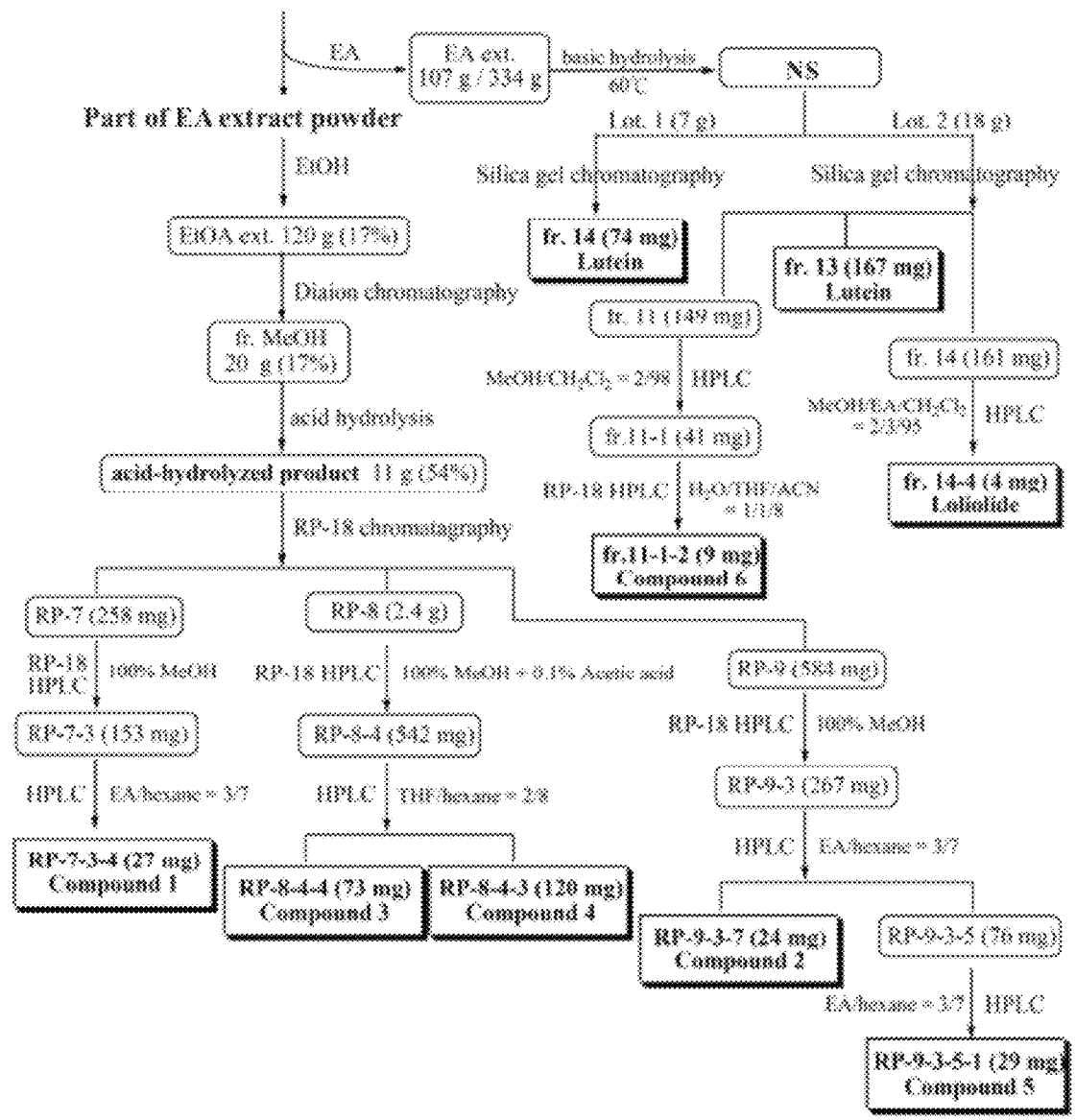
Referring to FIG. 1, flow chart for solution and purification of *Momordica charantia* active compounds.

The present invention uses ethyl acetate (EA) to extract compounds in *Momordica charantia* freeze dry powder to obtain an ethyl acetate extract and a residue, the ethyl acetate extract is further subject to alkaline hydrolysis for preparation of non-saponifiable fractions without fatty acid interference. The non-saponifiable fractions were separated and purified by GC-MS column chromatography and preparative HPLC and ER transactivation assay was used to detect active ingredients, thus obtained purified compounds with known structure such as lutein, loliolide and 5β,19-epoxycucurtita-6,24-diene-3β,23ξ-diol (compound 6). The residue of *Momordica charantia* is further extracted with ethanol to prevent low absorption of polar carbohydrate of test compounds by cells. It is also spectulated that compounds with smaller ligands are preferred for ER interaction, EtOH extract of *Momordica charantia* is subjected to acid hydrolysis and further purification process. Five novel cucurbitane-triterpenoid compounds are obtained. Structural identification of these novel cucurbitane-triterpenoid compounds indicated that they are: cucurbita-6,22(E),24-trien-3β-ol-19,5β-olide (compound 1), 5β,19-epoxycucurbita-6,22(E),24-trien-3β,19-diol (compound 2), 3β-hydroxycucurbita-5(10),6,22(E),24-tetraen-19-al (compound 3), 19-dimethoxycucurbita-5(10),6,22(E),24-tetraen-3β-ol (compound 4) and 19-nor-cucurbita-5(10),6,8,22(E),24-pentaen-3β-ol (compound 5). The present invention demonstrated that compound 1, 2, 5, 6, lutein and loliolide can activate ER (ERα and ERβ). When these compounds are co-administered with 17β-estradiol (E2), it is demonstrated that compound 1, 2, 3, 5, and 6 inhibited ERα and ERβ activation induced by E2 and luten and loliolide showed co-activation of ERα and ERβ.

Term Definition

The term "estrogenic active compound" used in the present invention is intended to mean natural or synthetic compounds having estrogenic activity, such as estrone (E1), 17β-estradiol (E2), 17α-ethinylestradiol (EE2); and 17β-estradiol (E2) are mainly used in the examples of the present invention.

The term "estrogen receptor" used in the present invention is intended to mean "human estrogen receptor" (ER) which mainly referred to ERα and ERβ with distinct distribution in human tissues. Estrogen receptors bind to human estrogens specifically and initiate estrogen regulating gene expression.

Materials and Methods

1. Estrogen Activity Analysis: Transactivation Assay for Estrogen Receptor

Plasmid pBKCMV containing GAL4-hERα (or ERβ) ligand binding domain (LBD) chimeric receptors and plasmid containing (UAS)$_4$-alkaline phosphatase (ALP) receptor gene were co-transfected into Chinese hamster cells (CHO-K1). Compounds with estrogenic activity would interact with estrogen-specific ER to induce the binding of GAL4 and upstream activation sequence (UAS)$_4$ specifically to initiate the expression of ALP gene. Therefore, the ALP activity can be used to determine whether the samples to be assayed have the estrogenic activity.

The CHO-K1 cell purchased from the Food Industry Research and Development Institute Taiwan with an accession number of CCRC 60006 were cultivated with medium containing 10% FBS and Ham's F12 nutrient mixture (GIBCOBRL). Cells in high confluence were plated onto 96-well culture plate the day before transfection. The plate was then washed to remove the serum during the day of transfection, followed by addition of two plasmid DNA, GAL4-hER☐ and (UAS)$_4$-ALP in the ratio of 1:1 together with Lipofectamine 2000 (GIBCOBRL) transfection agent and culture medium to form DNA-liposome complex for 5 hours. The sample to be assayed was added into the medium of transfected cells and cultivated for two days. The medium was aliquoted for ALP assay using 4-Nitrophenul phosphate disodium salt hexahydrate (pNPP) as the colorimetric substrate for alkaline phosphatase, and reading the absorbance of 405 nm. The known ER activator E2 at the concentration of 1 nM was used as the positive control.

2. Material Preparation 2-1. Preparation of *Momordica charantia* EA Extract

Twenty volumes of ethyl acetate (EA) were added into 200 gram of *Momordica charantia* freeze dry powder and stirred at room temperature for 16 to 20 hours. The solution was filtered for vacuum assisted fast filtration and the filtrates were collected. The powder retained on the membrane filter was extracted again with the same extraction process. The combined filtrates were evaporated in a rotary evaporator to remove the solvent and *Momordica charantia* ethyl acetate extract and residues were obtained. The yield of ethyl acetate extract was about 4%.

2-2 Preparation of Alkaline Hydrolysis Reaction and Non-Saponifiable Fraction (NS)

30 g of *Momordica charantia* ethyl acetate extract was dissolved in 5-fold (w/v) THF and the same volume of 40% NaOH solution and then stirred at 60° C. for 16 to 20 hours. The reaction solution was first evaporated in a rotary evaporator to remove the solvent THF then extracted with hexane/water (v/v, 1:1) for another 3 to 5 times. Hexane layer was collected and washed with water until neutral and then evaporated in a rotary evaporator to collect non-saponifiable fraction (NS). The amount of NS collected was 2.5% of ethyl acetate extract. HCl was added to the aqueous layer until the pH=2. Equal volume of ethyl acetate was added to perform extraction twice. The top ethyl acetate layer was washed with water until the mixture was neutral and then followed by evaporated under reduced pressure to obtain saponifiable fraction (S).

2-3. Preparation of EtOH Extract

The residues of *Momordica charantia* described in procedure 2-1 then immersed in 20-fold ethanol. The mixture was extracted and stirred for 16 to 20 hours twice. Combined extracts were evaporated in a rotary evaporator to remove solvent and thus obtained the EtOH extract. The yield of EtOH extract was about 18 to 20%.

2-4. Acid-Hydrolyzed Product

Acid Hydrolysis Reaction and Preparation of Acid-Hydrolyzed Product

Because EtOH extract of *Momordica charantia* contain fatty acids (very low polar) from ethyl acetate residual and highly polar sugars (for example, glucose), EtOH extract was subjected to reverse phase column chromatography (Diaion open column, packed with coarse particle size gel). A fraction of the eluents (as described later) was subjected to acid hydrolysis. 20.4 g of MeOH fraction (after removal of fatty acids and carbohydrates) was dissolved in 6-fold (120 ml) of de-ionized water. 4-fold volume 12 N HCl (80 ml) was added to final concentration of 15%. The solution was refluxed in water bath for one hour, and extracted with EA when the reaction solution was back to room temperature. The EA layer was washed with water until neutral and then followed by evaporation under reduced pressure to remove the solvent and an acid-hydrolyzed product (11 gram) was obtained. The yield of acid-hydrolyzed product was 54%.

3. Fraction and Purification of Compounds 3-1 Open Column Chromatography of NS

Weigh a certain amount of *Momordica charantia* NS extract and dissolved in minimum volume of hexane. The dissolved solution was loaded onto 10~15 fold weight of Silica gel (70~230 mesh) packed preparative silical column (silica gel filled about 60~70% of the glass column space, ID 3 cm, silical gel height 25 cm, equilibrated with n-hexane) for chromatography. The elution solution consisted of n-hexane and EA at different ratio, with the gradient conditions starting from 100% n-hexane, 1% EA/hexane, 2% EA, 5% EA, 10% EA, 20% EA, 30% EA, 50% EA and 100% EA. An aliquot of 250 ml column effluent was collected as a fraction. These fractions were analyzed with thin layer chromatography (TLC). Fractions that showed similar results were pooled. The fractions were further subjected to transactivation assay and NMR analysis as a tracking indicator for determination of bioactive compounds and for separation and purification.

NS fractions were separated by open column chromatography twice. In the first separation process, 7 gram of NS was passed through the column and each eluted fraction was assayed to examine distribution of ER activity. The fractions with biological activity were further purified with preparative High Performance Liquid Chromatography (HPLC) to collect single active compound. In the meantime of lot #1 separation, EA extract and NS preparation were continued. Active ingredients were found in the first lot of separation and purification processes, however, HPLC separation process had decreased recovery such that concentration of the active ingredients were too low for structure determination. Therefore, a second lot of NS fraction (18 g) were collected and subjected to column chromatography. With the results of lot #1 as reference, the eluted polar fractions with biological activity were analyzed with transactivation assay to determine their ER activity distribution. Further HPLC separation was conducted to purify a single compound.

3-2 Reverse Phase Column Chromatography (Diaion Chromatography) of Ethanol Extract Diaion gel was soaked in water to allow absorption of water. After sedimentation, gel was stirred for well suspension and then loaded onto glass column to prepare packed column (in ID 7 cm×Diaion gel Height 15 cm). Water in the column was then replaced with MeOH. When solvent in the column was 80% MeOH/$H_2O$, the column was ready for chromatography. EtOH extract of Momordical charantia (120 g) was divided into two parts. Each sample lot was first dissolved in a small amount of water and then loaded onto the column. When the sample was well absorbed into diaion gel, the gel was eluted with solvents starting from water (2 L), 50% MeOH/$H_2O$ (1.5 L), MeOH (1 L), acetone (2 L). Eluents from these four elution systems were collected and evaporated under reduced pressure, thus obtained water fraction, MeOH/water fraction, MeOH fraction and acetone fraction.

3-3 Reverse Phase Column Chromatography (RP-18 Chromatography) of Fractionation of Ethanol Extract Fractions and Acid Hydrolysate RP-18 gel was soaked in MeOH until equilibrium and then loaded onto glass column to prepare packed column (In ID 5 cm×RP-18 gel height 20 cm). When solvent in the column was equilibrated with 80% MeOH/$H_2O$, the column was ready for chromatography. There were two samples subjected to this reverse phase column chromatography, the MeOH/$H_2O$ fraction that obtained from Diaion column chromatography of ethanol extract and acid hydrolysate obtained from MeOH fraction under acid hydrolysis reaction. Samples were dissolved in small amount of water (small amount of MeOH could be added to improve solubility) and then loaded onto the packed column. When the sample was absorbed by the RP-18 gel, the column was first washed with 200 ml of 80% MeOH/$H_2O$ followed by MeOH elution. An aliquot of 250 ml of eluent was collected as a fraction. Each fraction was analyzed by TLC, and fractions that exhibited similar results were pooled.

3-4. Preparation of HPLC

After open column chromatography, screening of active compounds with transactivation assay and NMR analysis of compound structure in each fraction were conducted and preparative HPLC was used for further purification. Preferred elution system was determined according to the TLC study results. Samples ready for chromatography was dissolved in elution system and filtered through 0.22 μm membrane to remove un-dissolved particles. The eluted fractions were again subjected to TLC study and NMR spectrum analysis to confirm if single compound was collected. If not, the sample was purified further with HPLC of another elution system. When the collected fraction was justified as single compound, NMR, IR, Mass-spectrum were used to identify and deduce the structure, functional group and molecular weight of the compound.

Cucurbitane-Triterpenoid Compounds

EXAMPLE 1 cucurbita-6,22(E),24-trien-3β-ol-19,5β-olide (Compound 1)

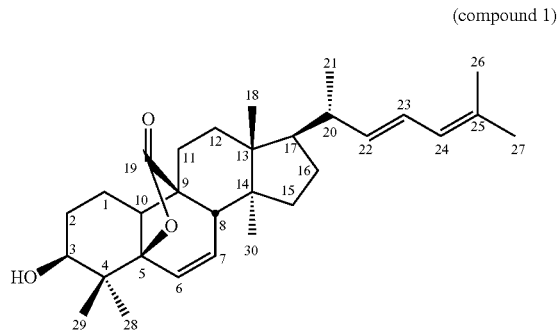

(compound 1)

Purification Steps of Compound 1 (Referring to FIG. 1)

MeOH fraction (20.4 g) of *Momordica charantia* EtOH extract that separated by Diaion chromatography column was subjected to acid hydrolysis to obtain an acid hydrolysate (11 g). The acid hydrolysate was separated with RP-18 column and eluted with MeOH. Totally 13 fractions (RP-1~13) were collected. RP-7 fraction (258 mg) was separated with RP-18 HPLC and eluted with 100% MeOH at flow rate of 2 mL/min. The fraction eluted at 9.7~11.3 min was collected to obtain RP-7-3 fraction (153 mg). This fraction was further purified with normal phase HPLC and eluted with 30% EA/70% hexane with a flow rate of 3 mL/min. The fraction eluted at 9.3 min was designated as RP-7-3-4 fraction (27 mg). The TLC results and NMR data justified that this was a single compound and designated as compound 1.

The RP-9 fraction (584 mg) of acid hydrolysate was subjected to RP-18 HPLC chromatography and eluted with 100% MeOH at flow rate of 3 mL/min. The fraction eluted at 6.7~7.5 min was collected to obtain RP-9-2 (47 mg). This fraction was further subjected to normal phase HPLC purification. The mobile phase was 30% EA/70% hexane with flow rate of 4 mL/min. The fraction eluted at 6.4 min was collected and designated as RP-9-2-4 (11 mg). NMR analysis exhibited that the compound had the same spectrum as RP-7-3-4 and thus designated as compound 1.

Structure Identification of Compound 1

Referring to FIG. 2 and FIGS. 9A~9E and Table 1a shown in later section, the results of secondary heteronuclear Multiple-Bond Correlation (HMBC), Nuclear Overhauser Effect Spectroscopy (NOESY), 1H Nuclear Magnetic Resonance Spectroscopy ($^1$H NMR), Distortionless Enhancement by Polarization Transfer (DEPT), Electron Impact Ionization (EIMS), High Resolution Mass Spectrometry (HRMS) and Fourier transform infrared spectroscopy (FTIR) of compound 1.

In the IR spectrum of compound 1, strong absorption appeared at 3501 and 1759 cm$^{-1}$, indicating that the compound contained hydroxyl and γ-lactone functional group; The molecular formula of compound 1 was deduced as C30H44O3, on the basis of HRMS ([M]+ m/z 452.3279) and $^{13}$C NMR (Table 1a). $^1$H and $^{13}$C NMR data (Table 1a) indicated the presence of six methyls singlet [$\delta_H$ 0.84, 0.92, 0.93, 1.25, 1.71, 1.73 (3H each, s), a secondary methyl [$\delta_H$ 1.02 (3H, d, J=6.5 Hz)] and one oxomethylene [$\delta_H$ 3.45 (1H, br s)]. Furthermore, $^1$H NMR signals for an allylic ABX system of cyclohexene [$\delta_H$ 5.17 (1H, dd, J=9.9, 2.2 Hz, H-6), 5.69 (1H, dd, J=9.9, 3.3 Hz, H-7), 2.51 (1H, dd, J=3.3, 2.2 Hz, H-8); $\delta_C$ 133.4 (d), 131.1 (d), 44.5 (d)] were found. Based on the above data, it was found that this compound was similar to a known compound karavilagenin D. It was elucidated that compound 1 was a cucurbitane-type triterpenoid compound.

Compound 1 shared similarity with known compound karavilagemin D in the A to D ring structure, and the only difference was the side chain structure of the D ring. On the basis of NMR data [$\delta_H$ 5.37 (1H, dd, J=15.0, 8.7 Hz, H-22), 6.14 (1H, dd, J=15.0, 10.8 Hz, H-23), 5.72 (1H, d, J=10.8 Hz, H-24), 1.71 and 1.73 (3H each, s); $\delta_C$ 138.1 (C-22), 124.4 (C-23), 125.1 (C-24), 133.1 (C-25), 18.2 (C-26), 25.9 (C-27)], side chain of compound 1 was deduced as E-form 1,1-dimethyl-4-alkyl-1,3-butadiene. Strong absorption was observed at 238 nm in UV spectrum, indicating presence of a double bond in the side chain. EIMS analysis showed a molecular ion peak at m/z 109 (100%), corresponding to the molecular formula C8H13, confirming proposed side chain structure. In HMBC spectrum (FIG. 2), correlations between H-27 ($\delta_H$ 1.73)/C-25 ($\delta_C$ 133.1) and C-24 ($\delta_C$ 125.1); H-24 ($\delta_H$ 5.72)/C-22 ($\delta_C$ 138.1) and C-23 ($\delta_C$ 124.4); H-21 ($\delta_H$ 1.02)/C-17 ($\delta_C$ 50.4), C-20 ($\delta_C$ 40.3) and C-22 ($\delta_C$ 138.1) were observed, which also confirmed the proposed side chain structure.

The relative configurations of methyl groups and other protons in the tetracyclic rings were determined by significant NOE correlations between H3-18 and H-8 & H3-20, H-3 & H3-29 and H-10 & H3-30 in the NOESY spectrum. Combining all results of karavilagenin D spectrum comparison and the results of HMBC, NOESY, UV, and IR spectrum of compound 1, the compound 1 was elucidated as cucurbita-6,22 (E),24-trien-3β-ol-19,5β-olide).

EXAMPLE 2

5β,19-epoxycucurbita-6,22(E),24-trien-3β,19-diol (compound 2)

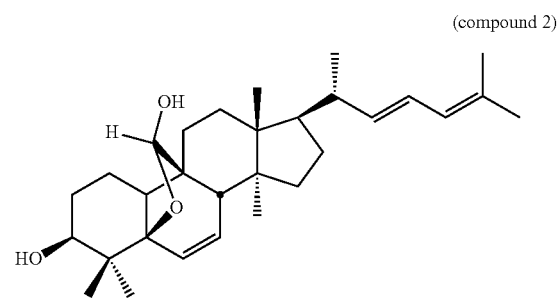

(compound 2)

Purification Steps of Compound 2 (Referring to FIG. 1)

RP-9 fraction was separated with RP-18 HPLC chromatography. The mobile phase was 100% MeOH and the flow rate was 3 ml/min. The fraction eluted at 7.5~8.8 min was collected to obtain RP-9-3 fraction (267 mg) which was further purified by a second HPLC. The mobile phase was 30% EA/70% hexane with a flow rate of 3 mL/min. The fraction eluted at 11.3 min was collected and designated as RP-9-3-7 fraction (24 mg). Results of TLC chromatography and NMR data justified that this was a single compound and designated as compound 2.

Structure Identification of Compound 2

Referring to FIG. 2, FIGS. 10A~10E and Table 1a, results of HMBC, NOESY, $^1$H NMR, DEPT, EIMS, HRMS and FTIR of compound 2 were exhibited. According to HMBC (m/z 454.3471) results, the molecular formula of compound 2 was deduced as C30H46O3. On the basis of IR spectrum, strong absorption appeared at 3421 cm$^{-1}$ and 1647 cm$^{-1}$, indicating that the compound contained hydroxyl functional group and a double bond. $^1$H and $^{13}$C NMR data (Table 1a) indicated the presence of six quaternary methyl groups, wherein two are double bond methyl group, one secondary methyl group, an oxygenated carbon and one allylic ABX system of cyclohexene. EI peak spectrum displayed absorption at 109 m/z and UV spectrum showed absorption at 238 nm, confirming the side chain structure C8H13. Comparing $^1$H and $^{13}$C NMR data of compound 1 and 2, it was found both compounds shared many similarities, with the exception that absorption of C-5 of γ-lactone group linked to C-19 ($\delta_C$ 181.5) shown in compound 1 spectrum was not found in compound 2 spectrum and compound 2 showed $\delta_H$ 5.12 (s) ($\delta_C$ 105.2) absorption. The allosteric orientation of hydroxyl group on the hemiacetal ring was endo-form, based on NOESY correlation (FIG. 2) of H-19 and H-1 (Mulholland et al., 1997; Li et al., 2007). On the basis of NOESY, IR and UV spectrum, the novel compound 2 was deduced as 5β,19-epoxycucurbita-6,22(E),24-trien-3β,19-diol.

EXAMPLE 3

3β-hydroxycucurbita-5(10),6,22(E),24-tetraen-19-al (compound 3)

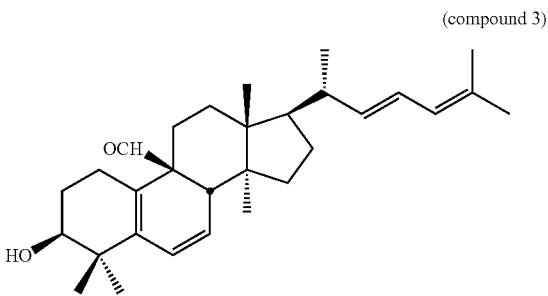
(compound 3)

Purification Steps for Compound 3 (Referring to FIG. 1)

RP-8 fraction (2.4 g) was separated with RP-18 HPLC chromatography. The mobile phase was 100% MeOH+0.1% acetic acid and the flow rate was 3 mL/min. The fraction eluted at 6.5~7.5 min and 7.8~8.7 min, respectively, were collected to obtain RP-8-2 fraction (488 mg) and RP-8-4 fraction (542 mg), which were further purified by a second HPLC. The mobile phase was 20% THF/80% hexane with a flow rate of 4 mL/min. The fraction eluted at 6.8 min was collected and designated as RP-8-2-4 fraction (45 mg) and RP-8-4-4 fraction (73 mg). NMR data justified that both fractions showed same spectrum and this single compound was designated as compound 3.

Structure of compound 3 changed easily; therefore, purification under similar separation condition was performed to remove spoiled ingredient. For storage of the sample minute amount of $NaHCO_3$ was supplemented and evaporated under reduced pressure at room temperature water bath to prevent spoilage of the compound.

Structure Identification of Compound 3

Referring to FIG. 2, FIGS. 11A~11E and Table 1a, the results of HMBC, $^1$H NMR, DEPT, EIMS, HRMS and FTIR analysis of compound 3 was exhibited.

On the basis of HRMS ([M]+ m/z 436.2970), the molecular formula of compound 3 was deduced as $C_{30}H_{44}O_2$. IR spectrum of compound 3 exhibited absorption at 3438 cm$^{-1}$, indicating presence of hydroxyl group. IR spectrum also showed absorption at 2723 and 1712 cm$^{-1}$, indicating presence of aldehyde group. $^1$H NMR and $^{13}$C NMR data (Table 1a) showed the presence of six methyl singlet [$δ_H$ 0.80, 0.90, 1.03, 1.05, 1.71, 1.72 (3H each, s)], one double split methyl [$δ_H$ 0.98 (3H, d, J=6.5 Hz)], a E-form 1,1,4-trialkylsubstituted buta-1,3-diene with one conjugated double bond on the side chain [$δ_H$ 5.35 dd (1H, dd, J=15.0, 8.7 Hz), 6.12 (1H, dd, J=15.0, 10.8 Hz), 5.72 (1H, d, J=10.8 Hz); $δ_C$ 138.3 (d), 124.3 (d), 125.1 (d), 132.9 (s)][UV λmax 239 nm], an absorption signal of cyclohexane [$δ_H$ 5.62 (1H, dd, J=10.0, 6.0 Hz), 6.04 (1H, d, J=. 10.0 Hz); $δ_C$ 126.2 (d), 126.8 (d)], and oxygenated tertiary carbon [$δ_H$ 3.50 (1H, dd, J=8.8, 2.9 Hz, H-3)].

Comparing $^1$H NMR and $^{13}$C NMR data of compound 3 and compound 1, it was found that side chain characteristics of compound 3 D ring was similar to that of compound 1, suggesting both compounds had the same side chain structure. Absorption at 273 nm as shown in UV spectrum and $^{13}$C NMR spectrum [$δ_C$ 126.8 (s) 137.7 (s), 126.2 (d), 126.8 (d)] data provided evidence of presence of cyclohexa-1,3-diene on B ring of compound 3. Based on the HMBC analysis (FIG. 2) of correlation of H-1 ($δ_H$ 2.14~2.26)/C-5 ($δ_C$ 137.7) & C-10 ($δ_C$ 126.8), H-6 ($δ_H$ 6.04)/C-5 ($δ_C$ 137.7) & C-7 ($δ_C$ 126.8) & C-8 ($δ_C$ 39.9) & C-10 ($δ_C$ 126.8), it was deduced that conjugated diene was between C-5, C-6, C-7 and C-10. The NMR data of the tetracyclic rings were in good agreement with those of cucurbita-5(10),6,23(E)-triene-3β,25-diol,(22) except for the signals of C-19. NMR absorption [$δ_H$ 9.23 (1H, s), $δ_C$ 202.3 (s)], indicating the presence of aldehyde group at C-19. In addition, HMBC spectrum data on correlation of $δ_H$ 9.23/C-8 ($δ_C$ 39.9), C-10 ($δ_C$ 126.8), C-11 ($δ_C$ 202.3) provided evidence of aldehyde group at C-19. Therefore, compound 3 was determined as 3β-hydroxycucurbita-5(10),6,22 (E),24-tetraen-19-al.

EXAMPLE 4

19-dimethoxycucurbita-5(10),6,22(E),24-tetraen-3β-ol (compound 4)

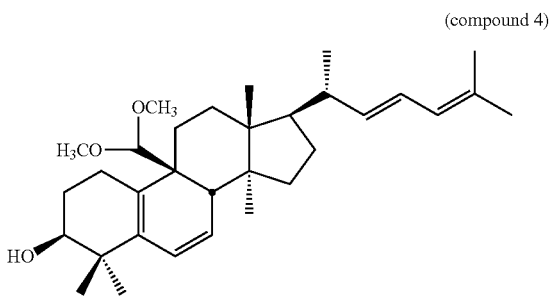
(compound 4)

Purification Steps of Compound 4 (Referring to FIG. 1)

Same separation steps for compound 3 were applied in compound 4 purification. RP-8-2 faction (488 mg) and RP-8-4 fraction (542 mg) were separated with RP-18 HPLC chromatography. The mobile phase was 20% THF/80% hexane and the flow rate was 4 mL/min. The fraction eluted at 5.7 min was collected to obtain RP8-2-3 fraction (78 mg) and RP-8-4-3 fraction (120 mg). NMR data justified that both fractions showed same spectrum and this single compound was designated as compound 4.

RP-9 fraction (584 mg) was separated with RP-18 HPLC. The mobile phase was 100% MeOH with flow rate of 3 mL/min. The fraction eluted at 8.8~10.4 min was collected to obtain RP-9-4 (204 mg). This fraction was again separated with HPLC again. The mobile phase was 25% EA/75% hexane with a flow rate of 3 mL/min. The fraction eluted at 7.9 min was collected to obtain RP-9-4-4 (44 mg). NMR data justified that spectrum of this compound was the same as RP-8-4-3 and this compound was designated as compound 4.

Identification of Compound 4

Referring to FIG. 2A, FIGS. 12A to 12E and Table 1b, HMBC, $^1$H NMR, DEPT, EIMS, HRMS and FTIR of compound 4 were displayed.

Figure 2:
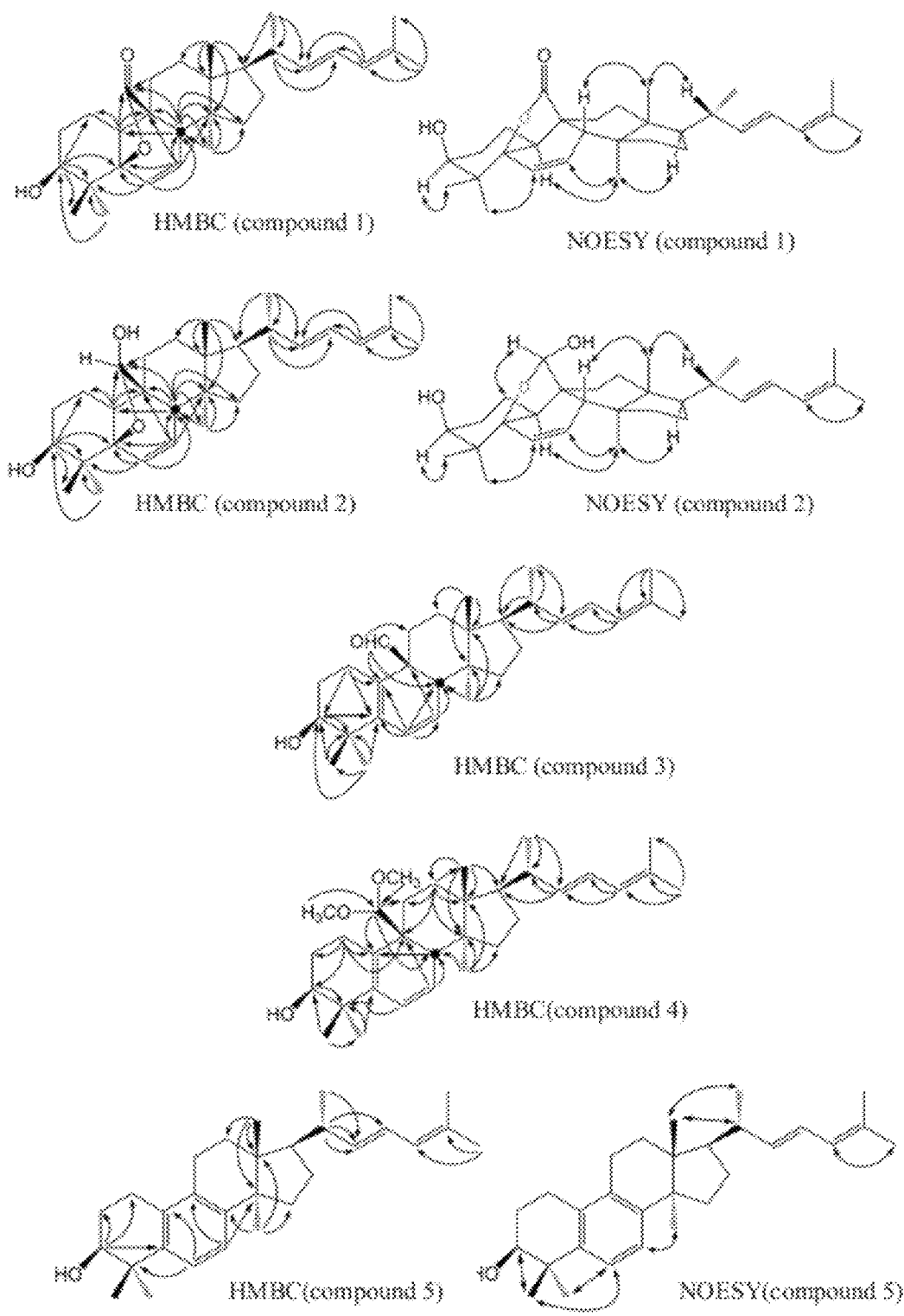
Referring to FIG. 2, relationship of HMBC and NOESY of compounds 1 to 5 purified from *Momordica charantia*.

On the basis of HRMS ([M]+ m/z 482.3767), the molecular formula of compound 4 was deduced as $C_{32}H_{50}O_3$ and its degree of unsaturation was 8. IR spectrum exhibited absorption at 3421 cm$^{-1}$, indicating presence of hydroxyl group. $^1$H NMR and $^{13}$C NMR data (Table 1b) indicated the presence of six methyls singlet, a secondary methyl, one cyclohexa-1,3-diene, one oxygenated tertiary carbon and one 1,3-butadiene, and one dimethyl acetal. UV spectrum showed absorption at 239 and 269 nm, indicating presence of conjugated diene. Comparison of $^1$H NMR and $^{13}$C NMR data showed that compound and compound 3 were similar, with exception of aldehyde group changed to dimethyl acetal on C19 of compound 3. NMR absorption [δ$_H$ 3.34, 3.44 (3H each, s), 3.99 (1H, s); δ$_C$ 58.1, 58.8, 112.3] indicated presence of two methoxy group and one tertiary carbon acetal structure (FIG. 2). Based on the 2D NMR spectrum, compound 4 was elucidated as 19-dimethoxycucurbita-5(10),6,22(E),24-tetraen-3β-ol.

EXAMPLE 5

19-nor-cucurbita-5(10),6,8,22(E),24-pentaen-3β-ol (compound 5)

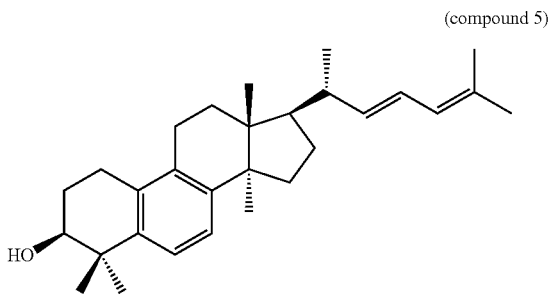

(compound 5)

Purification Steps of Compound 5 (Referring to FIG. 1)

Same separation steps for compound 3 were applied in compound 5 purification. RP-9-4 faction (204 mg) was separated with HPLC chromatography. The mobile phase was 25% EA/75% hexane and the flow rate was 3 mL/min. The fraction eluted at 7.2 min was collected to obtain RP9-4-3 fraction (15 mg). TLC results and NMR data justified that it was a single compound and this single compound was designated as compound 5.

Same separation steps for compound 2 were applied in compound 5 purification. RP-9-3 fraction (267 mg) was separated with HPLC. The mobile phase was 30% EA/70% hexane with flow rate of 3 mL/min. The fraction eluted at 7.3~8.0 min was collected to obtain RP-9-3-5 (76 mg). This fraction was again separated with HPLC. The mobile phase was 30% EA/70% hexane with a flow rate of 4 mL/min. The fraction eluted at 4.9 min was collected to obtain RP-9-3-5-1 (29 mg). NMR data justified that spectrum of this compound was the same as RP-9-4-3 and this compound was designated as compound 5.

Structure Identification of Compound 5

Referring to FIG. 2A, FIGS. 13A to 13E and Table 1b, HMBC, NOESY, $^1$H NMR, DEPT, EIMS, HRMS and FTIR of compound 5 were displayed. In the compound 5 IR spectrum, strong absorption appeared at 3012, 1606 and 1479 cm$^{-1}$, indicating the presence of aromatic ring. Absorption at 3415 cm$^{-1}$ suggested presence of hydroxyl group. On the basis of HRMS ([M]+ m/z 406.3241), the molecular formula of compound 5 was deduced as $C_{29}H_{42}O$ and its degree of unsaturation was nine. UV spectrum showed absorption at 239 nm, indicating conjugated diene absorption of 1,1,4-trialkylsubstituted buta-1,3-diene side chain. NMR data (Table 1b) indicated the presence of four quaternary methyl [δ$_H$ 0.65, 1.01, 1.26, 1.30 (3H each, s)], one secondary methyl [δ$_H$ 1.07 (3H, d, J=6.6 Hz)], two methyl [δ$_H$ 1.73, 1.74 (3H each, s)], one oxygenated tertiary carbon [δ$_H$ 3.72 (1H, dd, J=8.8, 2.9 Hz, H-3)], and three conjugated bond [δ$_H$ 5.44 (1H, dd, J=15.0, 8.4 Hz), 6.16 (1H, dd, J=15.0, 11.0 Hz) and 5.76 (1H, d, J=11.0 Hz)]。 $^{13}$C NMR data indicated 29 carbon signals, which could be classified as seven methyl, six secondary carbon, three quaternary carbon, six benzene ring, four double bond carbon and one oxygenated carbon.

Comparing $^1$H NMR and $^{13}$C NMR data (Table 1a and 1b) of compound 5 and compound 3 revealed that signals of the side chain of compound 5 were almost identical to that of compound 3, indicating same side chain structure of both compounds. A benzene ring structure existed in the tetracyclic skeleton of compound 5 which was judged from the two ortho-phenyl protons at δ$_H$ 7.11 (1H, d, J=8.1 Hz) and 6.86 (1H, d, J=8.1 Hz)), six $^{13}$C NMR absorption at δ$_C$ 122.8 (d), 123.8 (d), 140.6 (s), 132.0 (s), 132.6 (s) and 144.5 (s). In addition, 2D HMBC (FIG. 2) analysis showed correlation between H-6 (δ$_H$ 7.11)/C-4 (δ$_C$ 39.0), H-7 (δ$_H$ 6.86)/C-14 (δ$_C$ 50.2), and correlation of H-6 and H-28 NOESY, deduced that a benzene ring structure existed in the tetracyclic skeleton of compound 5. Based on the above data, compound 5 was elucidated as 19-nor-cucurbita-5(10), 6,8,22(E),24-pentaen-3β-ol.

EXAMPLE 6

5β,19-epoxycucurbita-6,24-dien-3β,23ξ-diol (compound 6)

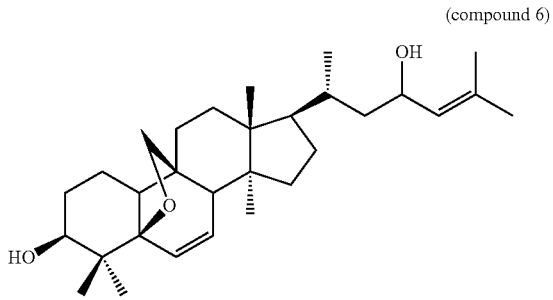

(compound 6)

Purification Steps of Compound 6 (Referring to FIG. 1)

NS fraction (18 g) of *Momordica charantia* was loaded onto silical chromography column and eluted with 50% EA/Hexane. The first 1 liter eluted solution was collected to obtain fraction 11 (149 mg). The fraction 11 was further separated with HPLC. The mobile phase was 2% MeOH/98% $CH_2Cl_2$ with flow rate of 4 mL/min. The fraction eluted at 6.4~8.3 min was collected to obtain fraction 11-1 (41 mg). This fraction was again separated with RP-18 HPLC. The mobile phase was $H_2O$/THF/ACN=1/1/8 with a flow rate of 4 mL/min. The fraction eluted at 6.5 min was collected to obtain fraction 11-1-2 (9 mg). TLC results and NMR data justified that this compound was a single compound and this compound was designated as compound 6.

Structure Identification of Compound 6

Comparing NMR data (Table 1b), it was found that compound 6 was identical as karavilagenin E, as confirmed by structure evidences such as HRMS ([M]+ m/z 456.3592) the molecular formula of compound 6 was deduced as C30H48O3 and its degree of unsaturation was 6. IR spectrum displayed absorption at 3423 cm$^{-1}$, indicating presence of hydroxyl group. $^1$H NMR and $^{13}$C NMR (Table 1b) data indicted the presence of six methyls singlet [δ$_H$ 0.84, 0.87, 0.87, 1.18, 1.67, 1.69 (3H each, s)], a double split methyl [δ$_H$ 0.95 (3H, d, J=6.5 Hz)], one cyclo-hex-diene [δ$_H$ 5.61 (1H, dd, J=9.8, 3.6 Hz), 6.02 (1H, dd, J=9.8, 2.0 Hz); δ$_C$ 131.5 (d), 131.7 (d)], one group alkenyl group [δ$_H$ 5.17 (1H, br d, J=8.4

Hz); $\delta_C$ 129.0 (d), 133.9 (s)], one oxygenated tertiary carbon [$\delta_H$ 3.38 (1H, br s, H-3)], one oxygenated secondary carbon [$\delta_H$ 3.49 (1H, d, J=8.4 Hz), 3.65 (1H, d, J=8.5 Hz); $\delta_C$ 79.9 (t)], and one proton of oxygenated tertiary carbon [$\delta_H$ 4.44 (1H, td, J=9.6, 3.1 Hz); $\delta_C$ 65.9 (d)]. 2D HMBC spectrum of three alkenyl group [$\delta_H$ 5.17], two singlet methyl group [$\delta_C$ 18.1 (s), 25.7 (s)], and oxygenated carbon [$\delta_C$ 65.9 (d)] supported evidence that side chain was 1,1-dimethyl-3-hydroxyl-4-alkylsubstituted butane. The 2D HMBC spectrum of exhibited the correlations between C19-methyl protons of oxygenated carbon [$\delta_H$ 3.49, 3.65] and C5-oxygenated quaternary carbon [$\delta_C$ 87.5 (s)], providing evidence that C-5 and C-19 is a ether group link. On the basis of spectrum data and 2D NMR, IR and UV spectrum, compound 6 was elucidated as 5β,19-epoxycucurbita-6,24-diene-3β,23ξ-diol.

TABLE 1a $^1$H NMR and $^{13}$C NMR Data of Compounds 1~3

| No. | 1 $\delta_C$ | 1 $\delta_H$ | 2 $\delta_C$ | 2 $\delta_H$ | 3 $\delta_C$ | 3 $\delta_H$ |
|---|---|---|---|---|---|---|
| 1 | 18.4 | 1.27-1.32 m, 1.59-1.65 m | 17.3 | 1.44-1.53 m | 23.9 | 2.14-2.26 m |
| 2 | 26.5 | 1.77-1.82 m | 27.0 | 1.71-1.80 m | 26.4 | 1.71-1.88 m |
| 3 | 75.3 | 3.45 br s | 76.1 | 3.39 br s | 75.1 | 3.50 dd (J = 8.8, 2.9) |
| 4 | 37.0 | | 37.2 | | 38.4 | |
| 5 | 85.4 | | 86.5 | | 137.7 | |
| 6 | 133.4 | 6.17 dd (J = 9.9, 2.2) | 132.9 | 6.04 dd (J = 9.8, 2.0) | 126.2 | 6.04 d (J = 10.0) |
| 7 | 131.1 | 5.69 dd (J = 9.9, 3.3) | 132.3 | 5.63 dd (J = 9.8, 3.5) | 126.8 | 5.62 d (J = 10.0, 6.0) |
| 8 | 44.5 | 2.51 dd (J = 3.3, 2.2) | 41.3 | 2.84 dd (J = 3.5, 2.0) | 39.9 | 2.63 br d (J = 6.0) |
| 9 | 51.1 | | 48.4 | | 52.2 | |
| 10 | 39.9 | 2.63 dd (J = 12.3, 5.8) | 40.5 | 2.44 dd (J = 10.6, 9.8) | 126.8 | |
| 11 | 21.7 | 1.72-1.78 m, 2.19-2.28 m | 23.1 | 1.68-1.77 m | 20.9 | 1.79-1.86 m |
| 12 | 29.8 | 1.22-1.25 m, 1.63-1.70 m | 30.5 | 1.61 m | 30.9 | 1.61-1.67 m |
| 13 | 45.1 | | 45.1 | | 45.0 | |
| 14 | 47.8 | | 48.0 | | 48.2 | |
| 15 | 33.2 | 1.26-1.33 m | 33.5 | 1.23-1.37 m | 31.6 | 1.15-1.19 m, 1.20-1.28 m |
| 16 | 27.8 | 1.29-1.36 m | 28.3 | 1.29-1.38 m | 27.9 | 1.22-1.30 m, 1.66-1.72 m |
| 17 | 50.4 | 1.48-1.56 m | 50.2 | 1.49 m | 50.5 | 1.49-1.56 m |
| 18 | 14.8 | 0.93 s | 14.9 | 0.89 s | 14.8 | 0.90 s |
| 19 | 181.5 | | 105.2 | 5.12 s | 202.3 | 9.23 s |
| 20 | 40.3 | 2.12-2.20 m | 40.3 | 2.14 m | 40.4 | 2.10-2.14 m |
| 21 | 20.5 | 1.02 d (J = 6.5) | 20.4 | 1.00 d (J = 6.6) | 20.5 | 0.98 d (J = 6.5) |
| 22 | 138.1 | 5.37 dd (J = 15.0, 8.7) | 138.4 | 5.38 dd (J = 14.9, 8.6) | 138.3 | 5.35 dd (J = 15.0, 8.7) |
| 23 | 124.4 | 6.14 dd (J = 15.0, 10.8) | 124.2 | 6.13 dd (J = 14.9, 10.6) | 124.3 | 6.12 dd (J = 15.0, 10.8) |
| 24 | 125.1 | 5.72 d (J = 10.8) | 125.1 | 5.73 d (J = 10.6) | 125.1 | 5.72 d (J = 10.8) |
| 25 | 133.1 | | 132.5 | | 132.9 | |
| 26 | 18.2 | 1.71 s | 18.2 | 1.71 s | 18.2 | 1.71 s |
| 27 | 25.9 | 1.73 s | 25.9 | 1.72 s | 25.9 | 1.72 s |
| 28 | 20.3 | 1.25 s | 20.4 | 1.19 s | 22.0 | 1.03 s |
| 29 | 23.5 | 0.92 s | 23.9 | 0.82 s | 25.8 | 1.05 s |
| 30 | 19.3 | 0.84 s | 19.7 | 0.85 s | 16.9 | 0.80 s |
| OCH$_3$ | | | | | | |
| OCH$_3$ | | | | | | |

TABLE 1b $^1$H NMR and $^{13}$C NMR Data of Compounds 4~6

| No | 4 $\delta_C$ | 4 $\delta_H$ | 5 $\delta_C$ | 5 $\delta_H$ | 6 $\delta_C$ | 6 $\delta_H$ |
|---|---|---|---|---|---|---|
| 1 | 24.2 | 2.07-2.14 m, 2.55 dt (J = 18.5, 5.9) | 24.1 | 2.52-2.68 m | 17.6 | 1.43-1.45 m |
| 2 | 26.6 | 1.66-1.69 m, 1.75-1.81 m | 26.6 | 1.91-1.96 m, 2.00-2.06 m | 27.4 | 1.77-1.79 m |
| 3 | 75.3 | 3.44* | 75.2 | 3.72 dd (J = 8.8, 2.9) | 76.2 | 3.38 br s |
| 4 | 38.1 | | 39.0 | | 37.2 | |
| 5 | 133.1 | | 140.6 | | 87.5 | |
| 6 | 125.8 | 6.07 d (J = 9.7) | 123.8 | 7.11 d (J = 8.1) | 131.7 | 6.02 dd (J = 9.8, 2.0) |
| 7 | 125.6 | 5.53 dd (J = 9.7, 6.2) | 122.8 | 6.86 d (J = 8.1) | 131.5 | 5.61 dd (J = 9.8, 3.6) |
| 8 | 39.8 | 2.40 d (J = 6.2) | 144.5 | | 52.0 | 2.32 br s |
| 9 | 45.1 | | 132.6 | | 45.5 | |
| 10 | 133.3 | | 132.0 | | 38.8 | 2.26 dd (J = 11.1, 7.1) |
| 11 | 18.4 | 1.79-1.87 m | 24.1 | 2.52-2.68 m | 23.6 | 1.45-1.49 m, 1.70-1.75 m |
| 12 | 31.3 | 1.48-1.54 m | 30.9 | 1.91-2.03 m | 30.9 | 1.60 m |
| 13 | 45.4 | | 44.0 | | 45.4 | |
| 14 | 48.0 | | 50.2 | | 48.7 | |
| 15 | 32.1 | 1.08-1.12 m, 1.17-1.22 m | 32.1 | 1.63-1.70 m, 1.75-1.85 m | 33.1 | 1.28-1.31 m |
| 16 | 28.1 | 1.18-1.24 m, 1.63-1.67 m | 28.6 | 1.42-1.46 m, 1.90-1.94 m | 28.2 | 1.95 m, 1.38-1.40 m |
| 17 | 50.4 | 1.42-1.47 m | 50.4 | 1.67-1.73 m | 50.9 | 1.38-1.48 m |
| 18 | 14.6 | 0.88 s | 16.2 | 0.65 s | 14.9 | 0.87 s |

TABLE 1b-continued $^1$H NMR and $^{13}$C NMR Data of Compounds 4~6

| No | 4 δ$_C$ | 4 δ$_H$ | 5 δ$_C$ | 5 δ$_H$ | 6 δ$_C$ | 6 δ$_H$ |
|---|---|---|---|---|---|---|
| 19 | 112.3 | 3.99 s | | | 79.9 | 3.65 d (J = 8.5), 3.49 d (J = 8.5) |
| 20 | 40.4 | 2.07-2.14 m | 40.9 | 2.17 m | 32.6 | 1.65-1.72 m |
| 21 | 20.5 | 0.96 d (J = 6.5) | 20.7 | 1.07 d (J = 6.6) | 18.6 | 0.95 d (J = 6.4) |
| 22 | 138.8 | 5.34 dd (J = 15.0, 8.8) | 138.6 | 5.44 dd (J = 15.0, 8.4) | 44.4 | 1.58-1.66 m, 1.02 td (J = 10.2, 3.1) |
| 23 | 123.9 | 6.09 dd (J = 15.0, 10.8) | 124.3 | 6.16 dd (J = 15.0, 11.0) | 65.9 | 4.44 td (J = 9.6, 3.1) |
| 24 | 125.2 | 5.70 d (J = 10.8) | 125.2 | 5.76 d (J = 11.0) | 129.0 | 5.17 br d (J = 8.4) |
| 25 | 132.5 | | 132.8 | | 133.9 | |
| 26 | 18.2 | 1.69 s | 18.2 | 1.73 s | 18.1 | 1.78 d (J = 1.0) |
| 27 | 25.8 | 1.70 s | 25.9 | 1.74 s | 25.7 | 1.69 br s |
| 28 | 22.4 | 1.02 s | 25.3 | 1.26 s | 20.5 | 1.18 s |
| 29 | 25.8 | 1.01 s | 29.3 | 1.30 s | 24.5 | 0.87 s |
| 30 | 16.2 | 0.65 s | 28.2 | 1.01 s | 20.0 | 0.84 s |
| OCH$_3$ | 58.1 | 3.44 s | | | | |
| OCH$_3$ | 58.8 | 3.34 s | | | | |

*overlap

EXAMPLE 7

Estrogenic Activity of Compounds 1~6

The curcubitane-riterpenoid compounds (compounds 1~6) described above were assayed for their transactivation. The results showed that the reporter gene ALP activity increased as the concentration of compound 1, 2, 5, and 6 increased (referring to FIGS. 3A and 3B). Among these four compounds, compound 6 had higher activation capability. Maximum activation effect was observed at 22 μM for ERα (30% of E2) and ERβ (23% of E2). Activation capability of compound 1, 2, and 5 was only half of compound 6. Maximum activation for ERα of these three compounds was 12%, 15%, and 15% of E2 respectively and for ERβ, 10%, 8% and 9% of E2 respectively. Because compound 3 and 4 showed cytotoxicity (maximum tolerable for cells was only 2 μM), thus there was no significant activation of ERα and ERβ of compound 3 and 4 under tested condition.

Figure 3:
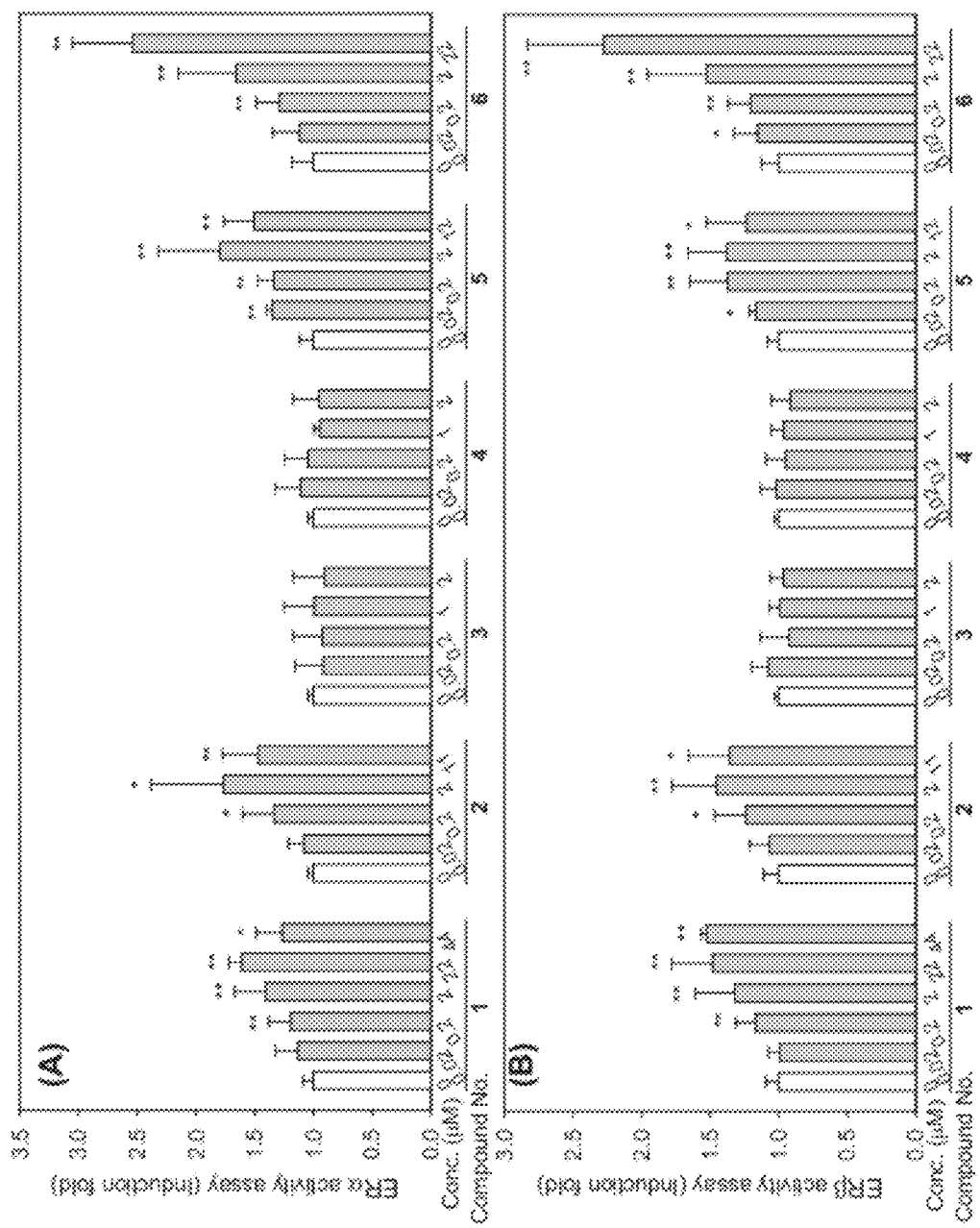
Referring to FIGS. 3A to 3B, dose response of compounds 1 to 6 for the transactivation of ERα and ERβ.
Figure 4:
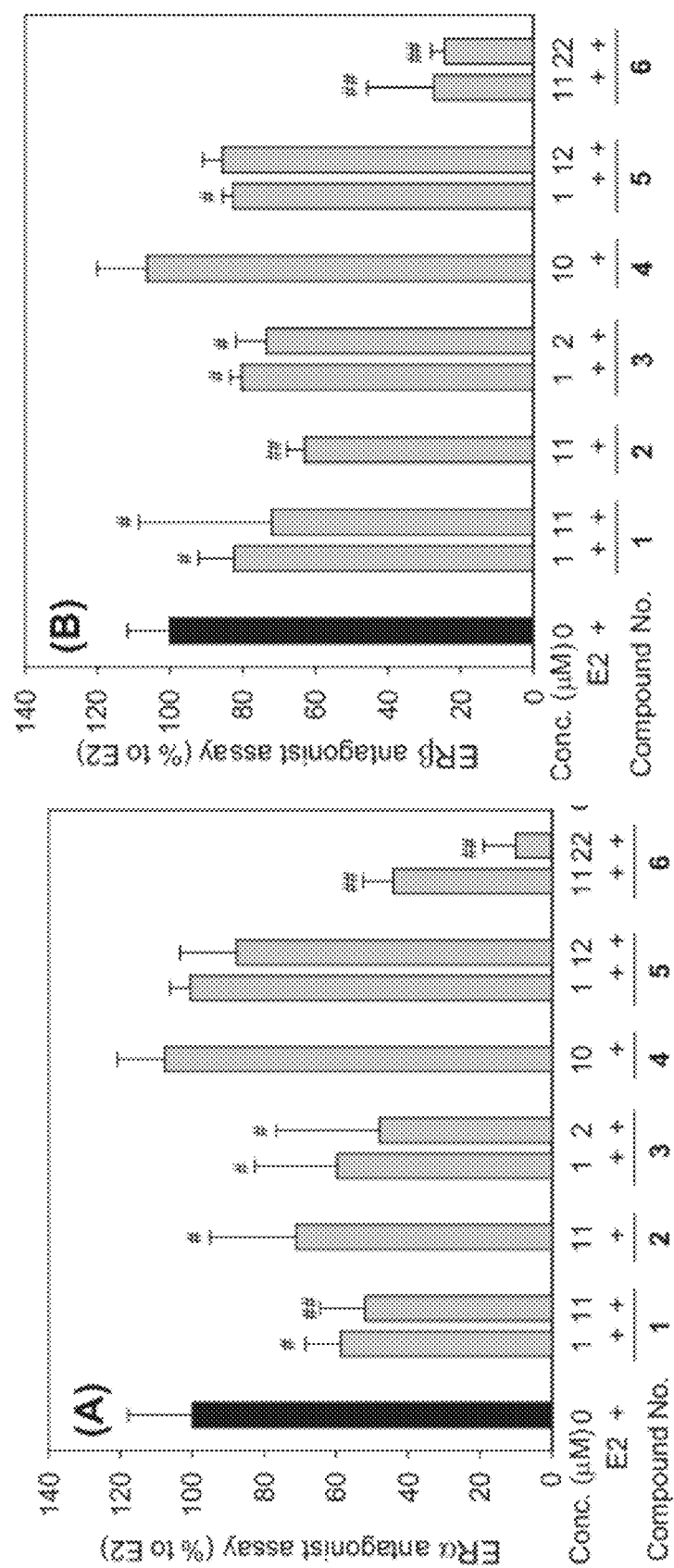
Referring to FIGS. 4A to 4B, dose response of compounds 1 to 6 and 1 nM E2 combination treatment for the transactivation of ERα and ERβ.

Error bar in FIGS. 3 and 4 represented value average of means±SD of fold activation from three independent experiments. When 1 nM E2 was used as the positive control, effect of these compounds for ERα activation was 6.2±1.3 fold and for ERβ activation was 6.5±1.1 fold. * label represented significant difference after student t test (p<0.01) versus blank vehicle.

Compounds 1~6 were treated with 1 nM E2 separately to analyze their effect on E2 activation for ER transactivation (referring to FIGS. 4A and 4B). The results showed that compound 1, 2, 3 and 6 had antagonistic activity toward ER. As the concentration of compound increased, ERα and ERβ activation decreased due to E2. Compound 1 and 2 at concentration of 11 μM could inhibit E2 activation of ERα and ERβ to 60~70%. At concentration of 2 μM, compound 3 reduced ALP activity to that were 48% and 73% that of ERα and ERβ. At concentration of 22 μM, compound 6 reduced ALP activity to 10% and 24% that of ERα and ERβ, which demonstrating most significant reduction of E2 induced activation of ER. At concentration of 1 μM, compound 5 showed slight inhibition of E2 induced activation of ERβ (83% of E2, p<0.05). Compound 4 had no effect on E2 induced transactivation of ERα and ERβ.

Values shown in FIGS. 4A and 4B selected E2 activation fold as 100% and activation fold of the blank vehicle as 0%. Error bar represented value average of means±SD of fold activation from three independent experiments. # and ## labels represented significant difference after t-test (p<0.05 (#) and p<0.01 (##)) with addition of E2.

EXAMPLE 8

Lutein

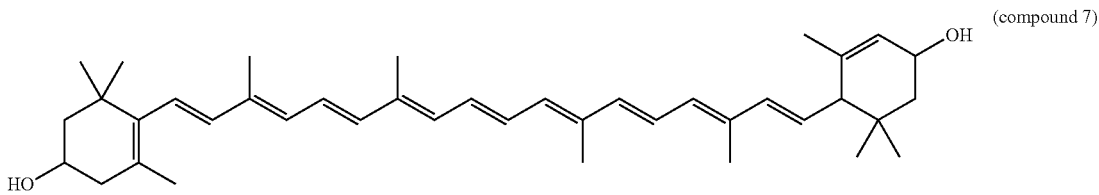 [SMILES: CC1=CC(O)CC(C)(C)C1/C=C/C(C)=C/C=C/C(C)=C/C=C/C=C(C)/C=C/C=C(C)/C=C/C1=C(C)CC(O)CC1(C)C]

(compound 7)

Purification Process (Referring to FIG. 1)

NS of lot 1 of *Momordica charantia* (7 g) was separated by silica gel column chromatography with 30% EA/hexan as mobile phase. 0.5 L eluent was collected as fraction 13, fraction 14 and fraction 15. The fraction 14 (74 mg) was confirmed to be lutein after NMR and MS analysis.

NS of lot 2 of *Momordica charantia* (18 g) was separated by silica gel column chromatography with 50% EA/hexan as mobile phase. The first 1.5 L of eluent was collected as fraction 11 (149 mg) and fraction 12 (124 mg). Further 0.5 L eluent was collected as fraction 13 (156 mg), and the last 1 L of eluent was collected as fraction 14 (161 mg). The fraction 13 was confirmed to be lutein after NMR analysis.

Fraction 12 of Lot 2 NS was separated with preparative RP-18 HPLC and the fraction 12-4 (3 mg. Mobile phase: $H_2O/THF/ACN=5/10/85$; flow rate: 5 mL/min, peak showed at 10.1 min) was obtained. The fraction 14 was separated with HPLC and obtained fraction 14-3 (4 mg, mobile phase: $MeOH/EA/CH_2Cl_2=2/3/95$, flow rate 3 mL/min, eluted at 8.1 min). This fraction was also identified as lutein.

EXAMPLE 9

Estrogenic Activity of Lutein

Figure 5:
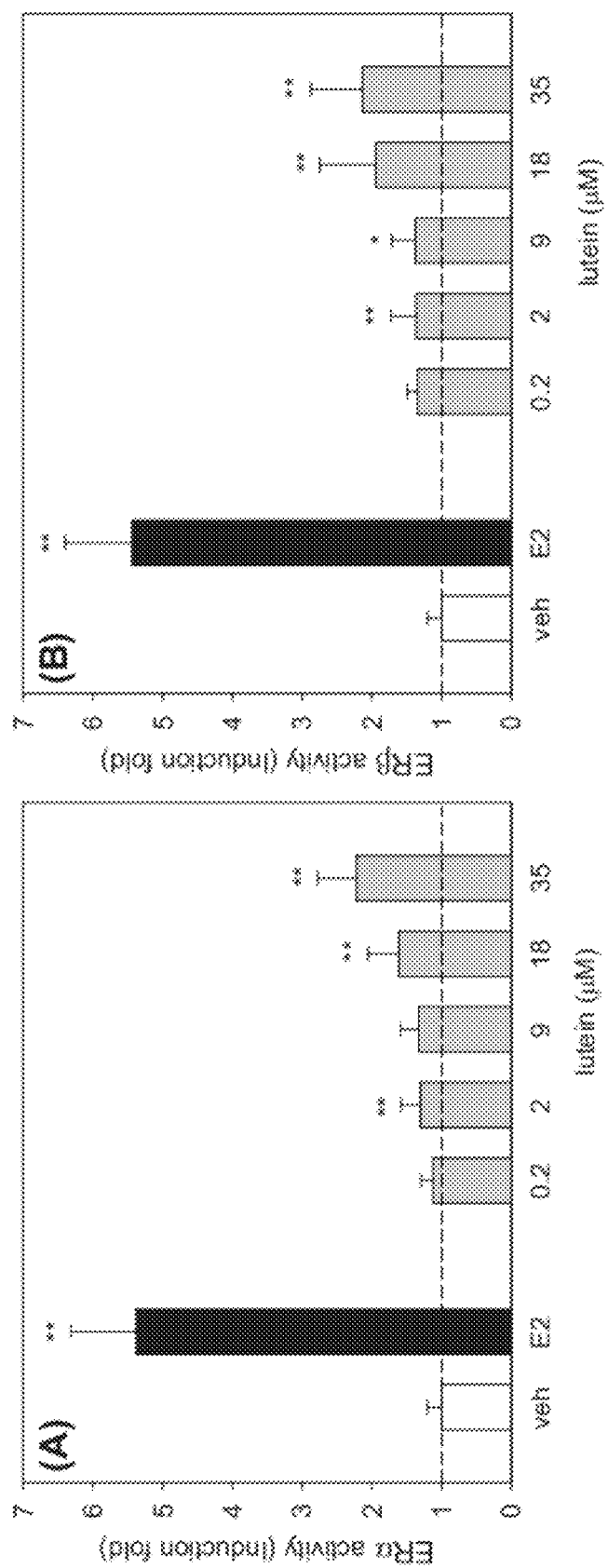
Referring to FIGS. 5A to 5B, dose response of leutein for the transactivation of on ERα and ERβ.

Purified lutein was determined for estrogenic activity using transactivation assay. The results indicated that the ALP activities were enhanced with the increase of concentration of the compound in a dose dependent manner. When the concentration reached at 35 μM, the maximum activation of the ERα and ERβ was achieved (29% and 26% that of E2) as shown in FIGS. 5A and 5B. The EC50 value for ERα and ERβ were 17.5 μM and 11.8 μM, respectively.

The results of FIGS. 5A and 5B was represented as means±SD of triplicate wells from three independent experiments. * and ** labels represented significant difference after t-test ($p<0.05$ (*) and $p<0.01$ (**)) versus blank vehicle.

Purified lutein and 1 nM E2 were co-added into the cells of test system. The results showed the activation of ERα and ERβ due to estrogen was enhanced by lutein. When the concentration of lutein reached at 18 the maximum activation of the ERα and ERβ was achieved (141% and 166% that of E2) as shown in FIGS. 6A and 6B.

Figure 6:
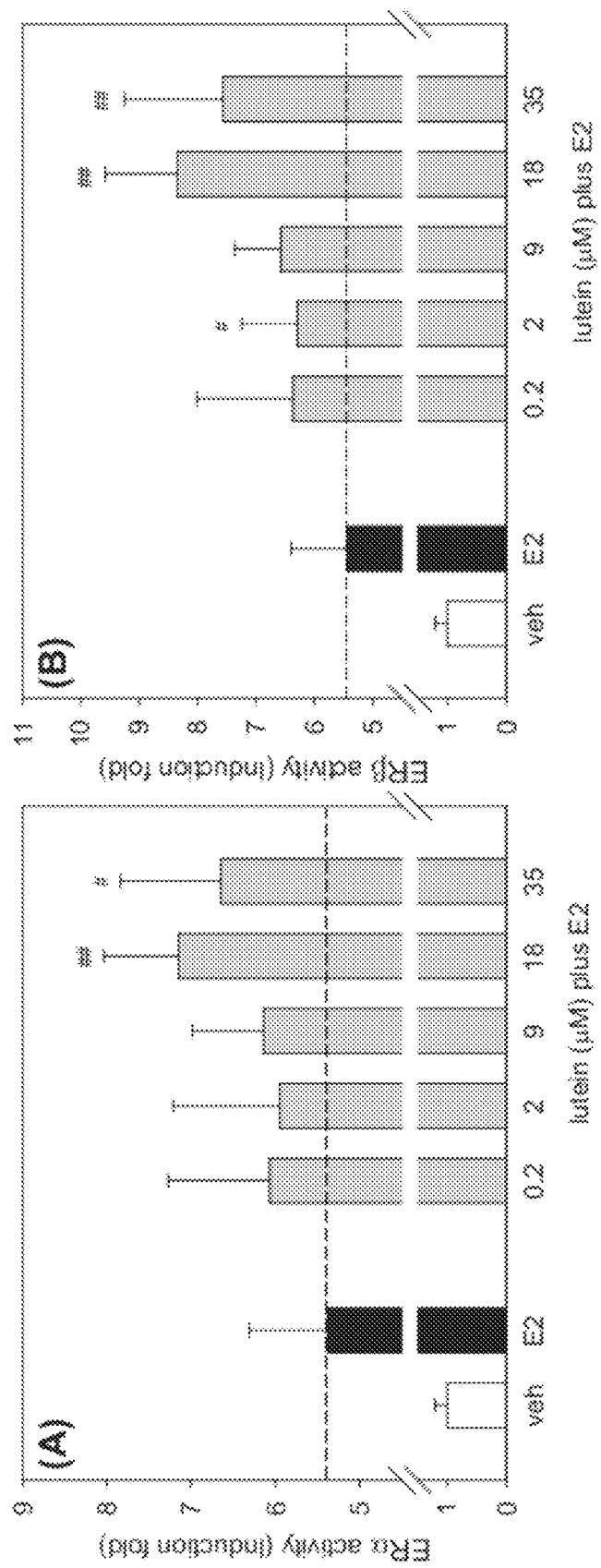
Referring to FIGS. 6A to 6B, dose response of leutein and 1 nM E2 combination treatment for the ransactivation of ERα and ERβ.

The results of FIGS. 6A and 6B was represented as means±SD of triplicate wells from three independent experiments. * and ** labels represented significant difference after t-test ($p<0.05$ (#) and $p<0.01$ (##)) with addition of E2 as positive control.

EXAMPLE 10 Loliolide

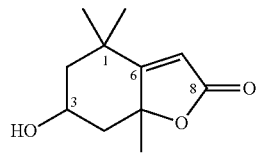

(compound 8)

Purification Steps (Referring to FIG. 1)

Fraction 14 (161 mg) of Lot 2 NS was separated with normal phase HPLC and the fraction 14-4 (4 mg, Mobile phase: $MeOH/EA/CH_2Cl_2=2/3/95$; flow rate: 3 mL/min, peak showed at 8.5 min) was obtained. This fraction was analyzed using NMR. The NMR results and GC-MS spectrum comparison identified the compound as loliolide.

Identification of Loliolide

Loliolide: $C_{11}H_{16}O_3$, $^1H$ NMR (400 MHz, $CDCl_3$): δ 5.67 (1H, s, H-7), 4.31 (1H, m, H-3), 2.43 (1H, ddd, J=14.1, 2.6, 2.6 Hz, H-4β), 1.95 (1H, ddd, J=14.5, 2.7, 2.7 Hz, H-2β), 1.76 (3H, s, 5-$CH_3$), 1.76 (1H, dd, J=14.1, 4.0 Hz, H-4α), 1.51 (1H, dd, J=14.5, 3.7 Hz, H-2α), 1.45 (3H, s, 1α-$CH_3$), 1.27 (3H, s, 1β-$CH_3$). $^1H$ NMR results were the same as scientific publications.

EXAMPLE 11

Estrogenic Activity of Loliolide

Purified loliolide was determined for estrogenic activity using transactivation assay. The results indicated that the ALP activities were enhanced with the increase of concentration of the compound in a dose dependent manner. When the concentration of loliolide reached at 102 the maximum activation of the ERα was achieved (24% of E2). When the concentration of loliolide reached at 51 μM, the maximum activation of the ERβ was achieved (20% of E2), referring to FIGS. 7A and 7B. The EC50 value for ERα and ERβ were 14.2 μM and 16.7 μM, respectively.

Figure 7:
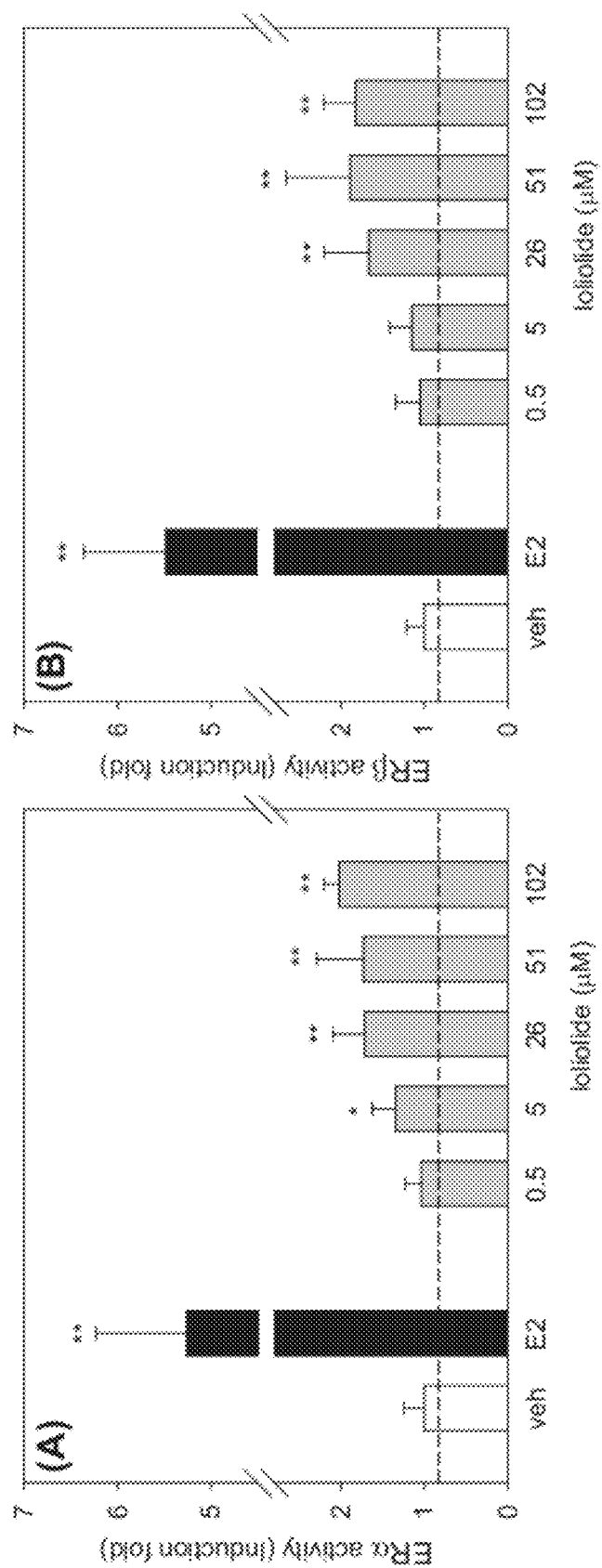
Referring to FIGS. 7A to 7B, dose response of loliolide for the transactivation of ERα and ERβ.

The results of FIGS. 7A and 7B was represented as means±SD from three independent experiments. * and ** labels represented significant difference after t-test ($p<0.05$ (*) and $p<0.01$ (**)) with addition of E2.

Purified lutein and 1 nM E2 were co-added into the cells of test system. The results showed the activation of ERα and ERβ due to estrogen was enhanced by loliolide. When the concentration of loliolide reached at 102 μM, the maximum activation of the ERα was achieved (146% of E2). When the concentration of loliolide reached at 51 μM, the maximum activation of the ERβ was achieved (145% of E2), referring to FIGS. 8A and 8B.

Figure 8:
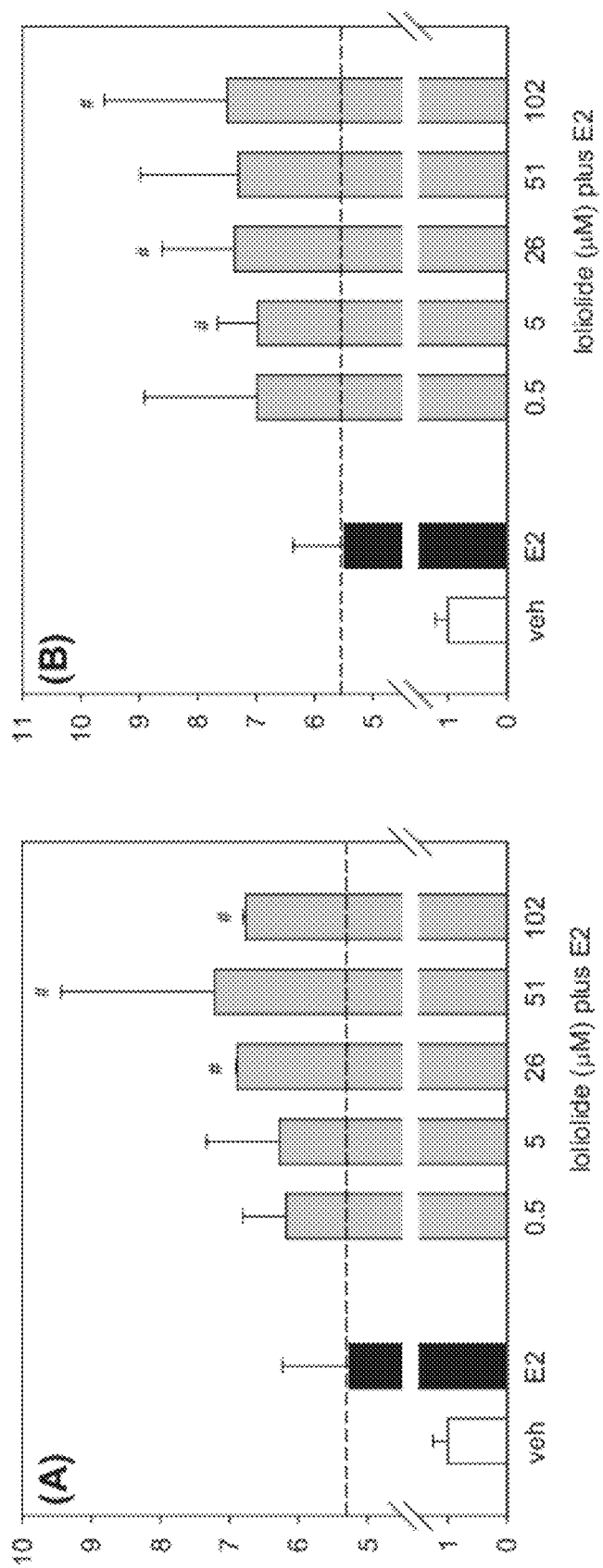
Referring to FIGS. 8A to 8B, dose response of loliolide and 1 nM E2 combination treatment for the transactivation of ERα and ERβ.
Figure 9:
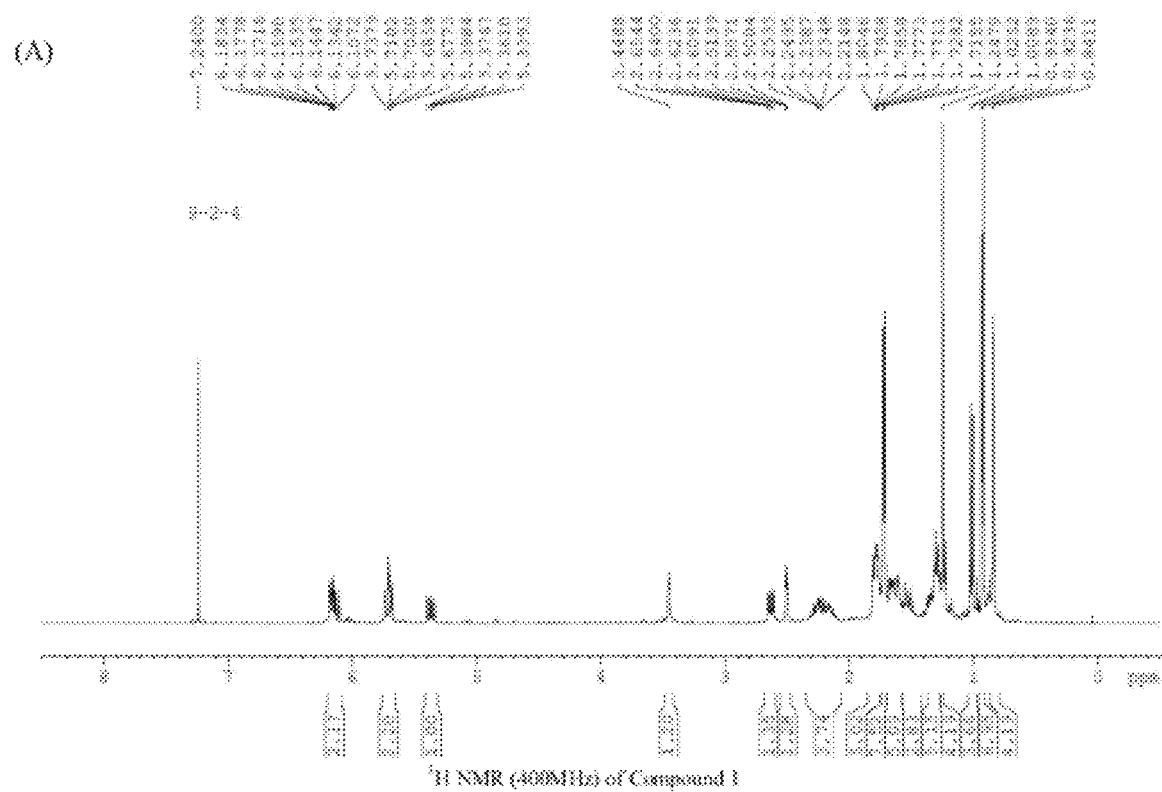
Referring to FIGS. 9A to 9E, $^1$H NMR、DEPT、EIMS、HRMS and FTIR spectrum of compound 1.
Figure 9:
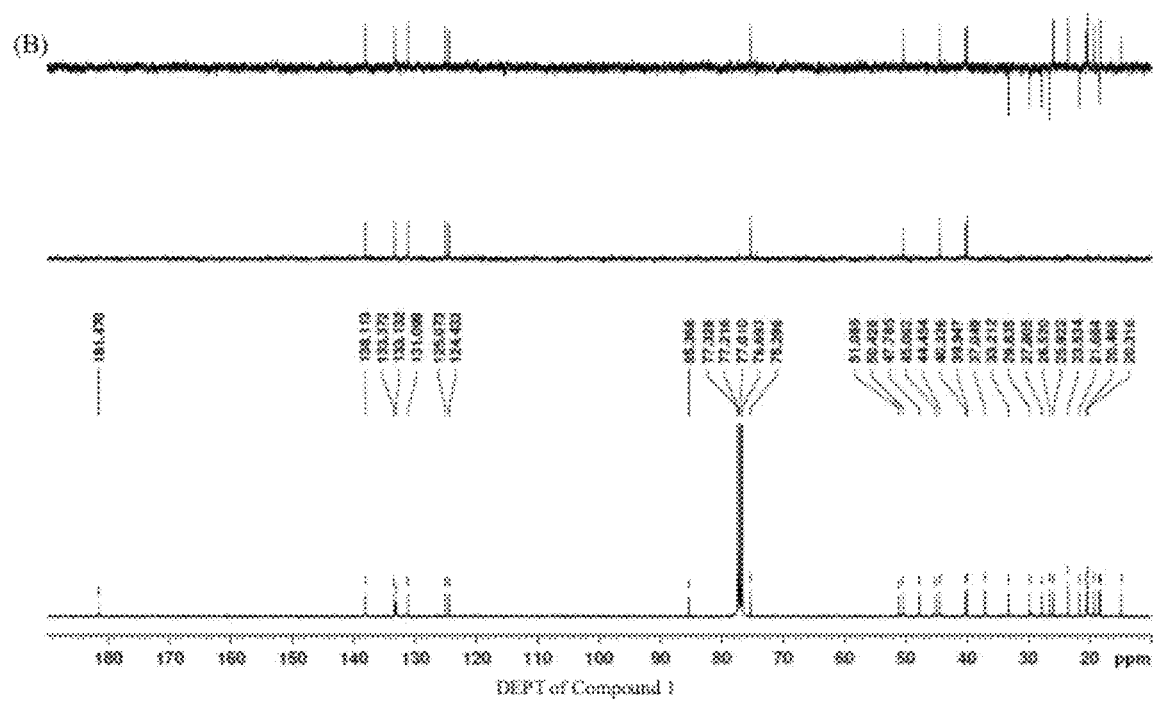
Figure 9:
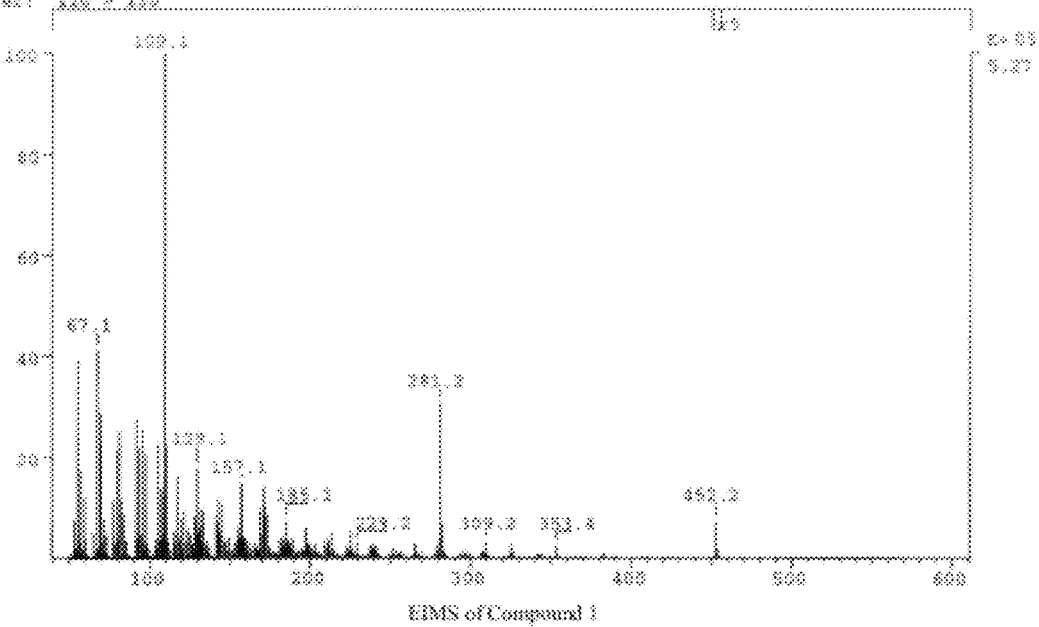
Figure 9:
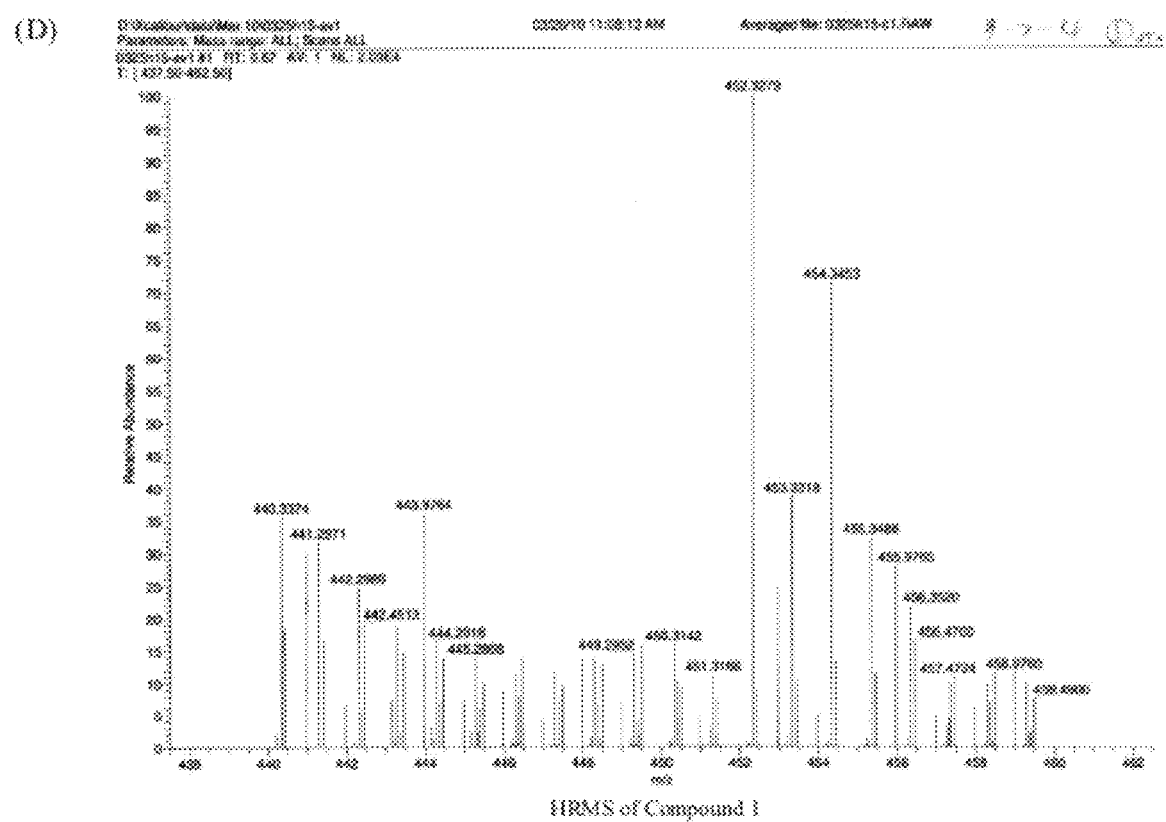
Figure 9:
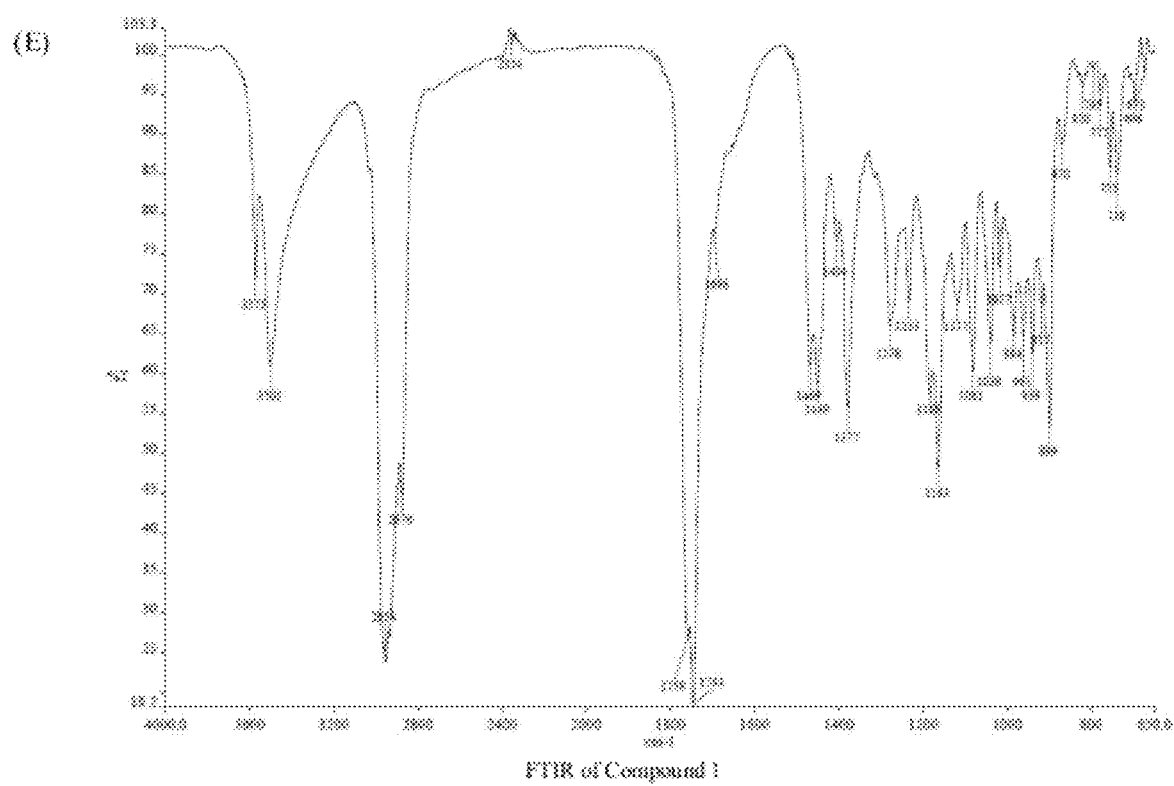
Figure 10:
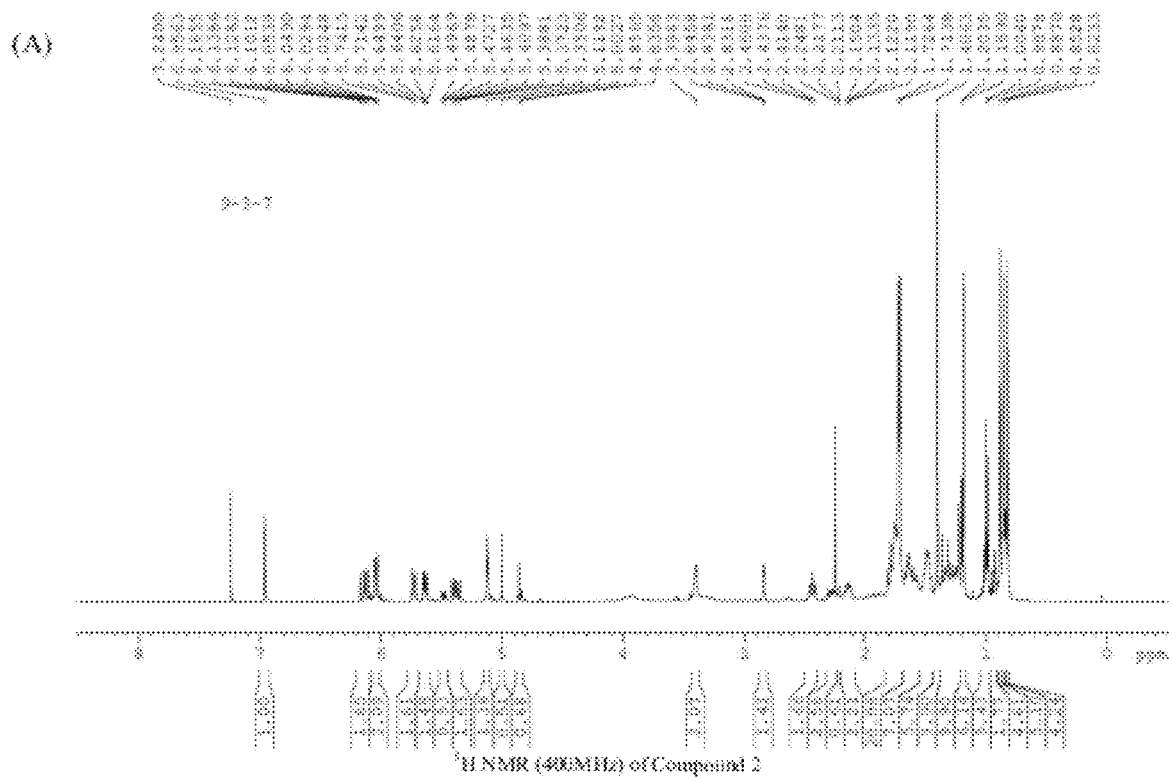
Referring to FIGS. 10A to 10E, $^1$H NMR、DEPT、EIMS、HRMS and FTIR spectrum of compound 2.
Figure 10:
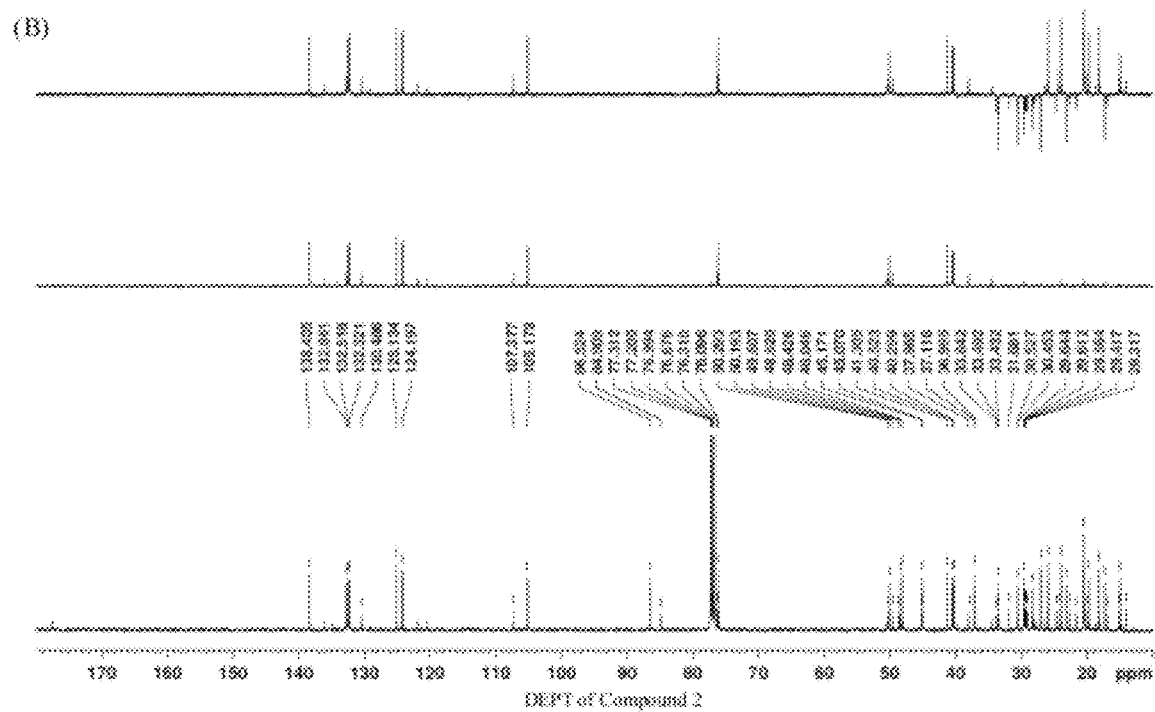
Figure 10:
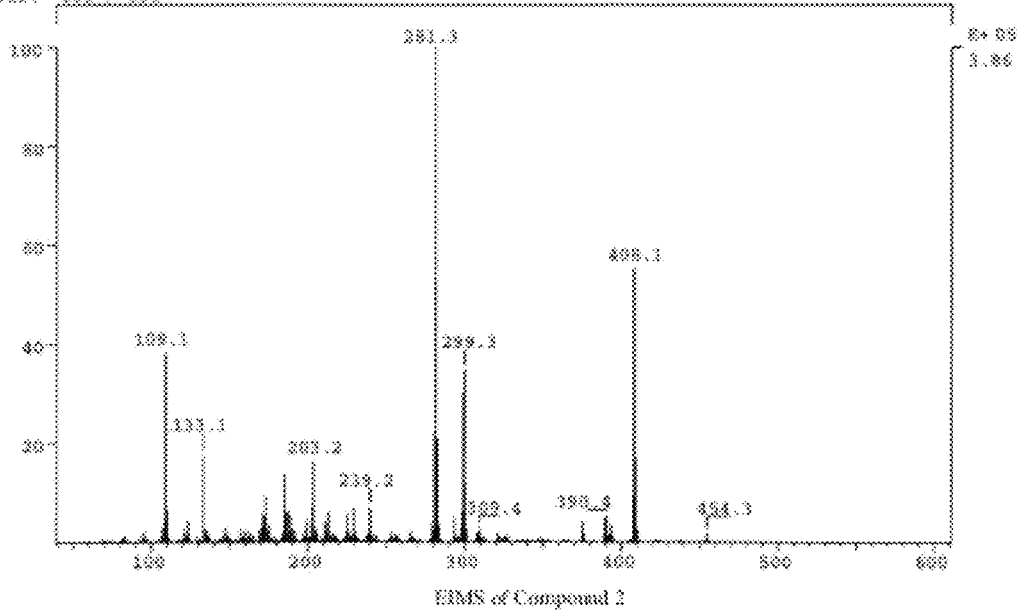
Figure 10:
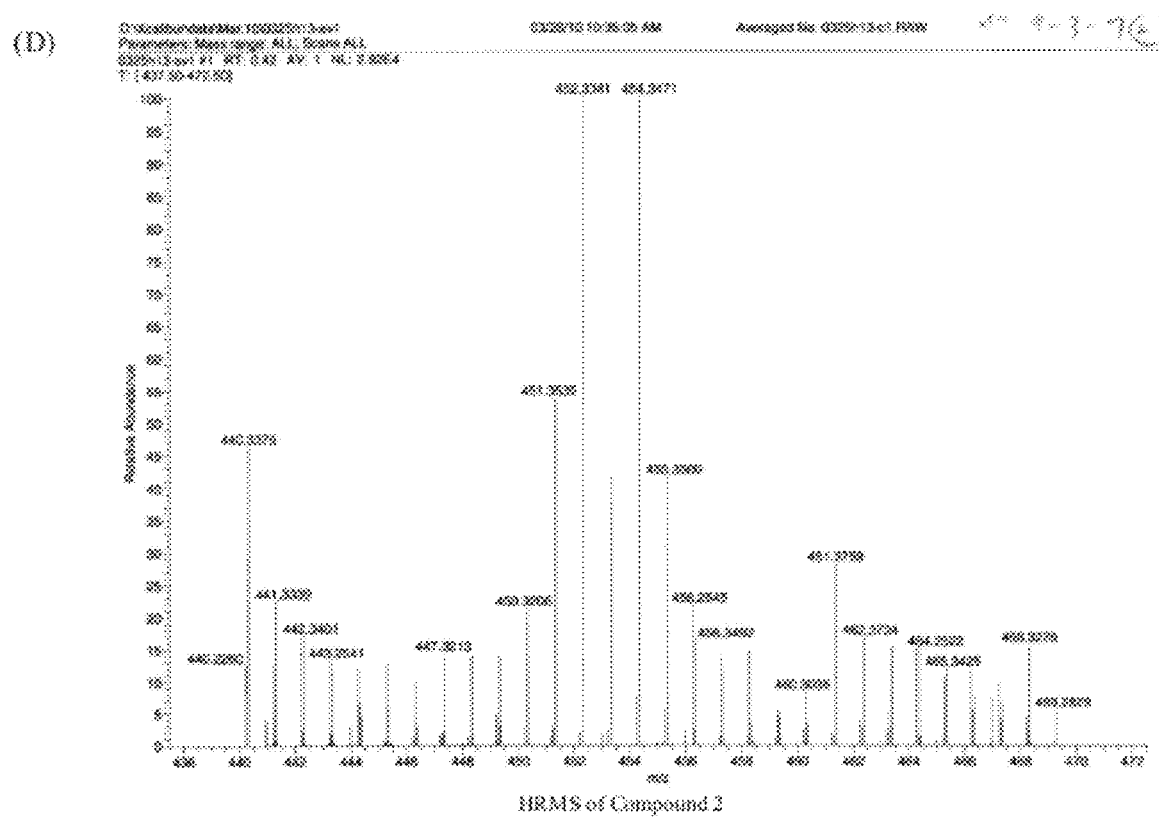
Figure 10:
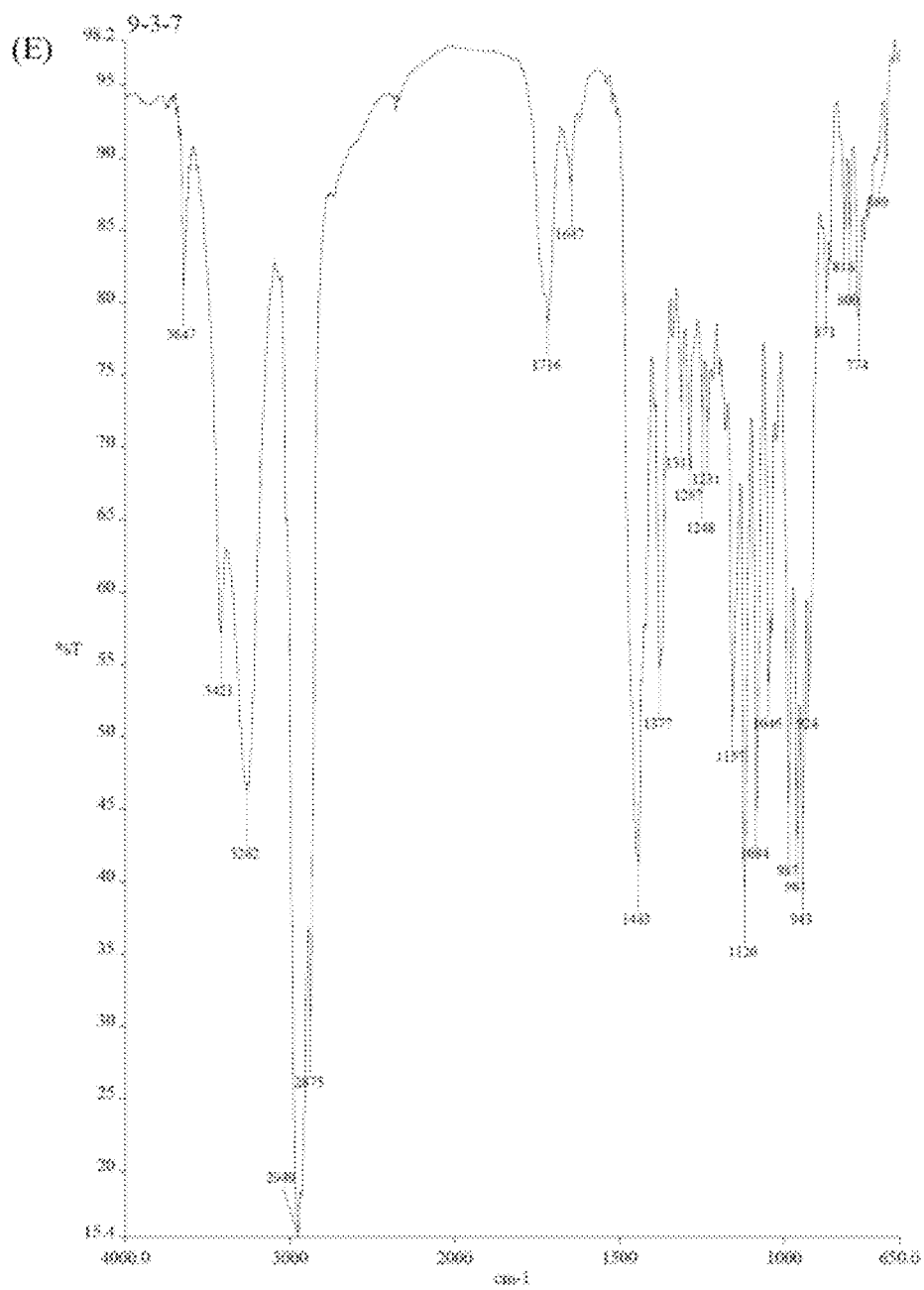
Figure 11:
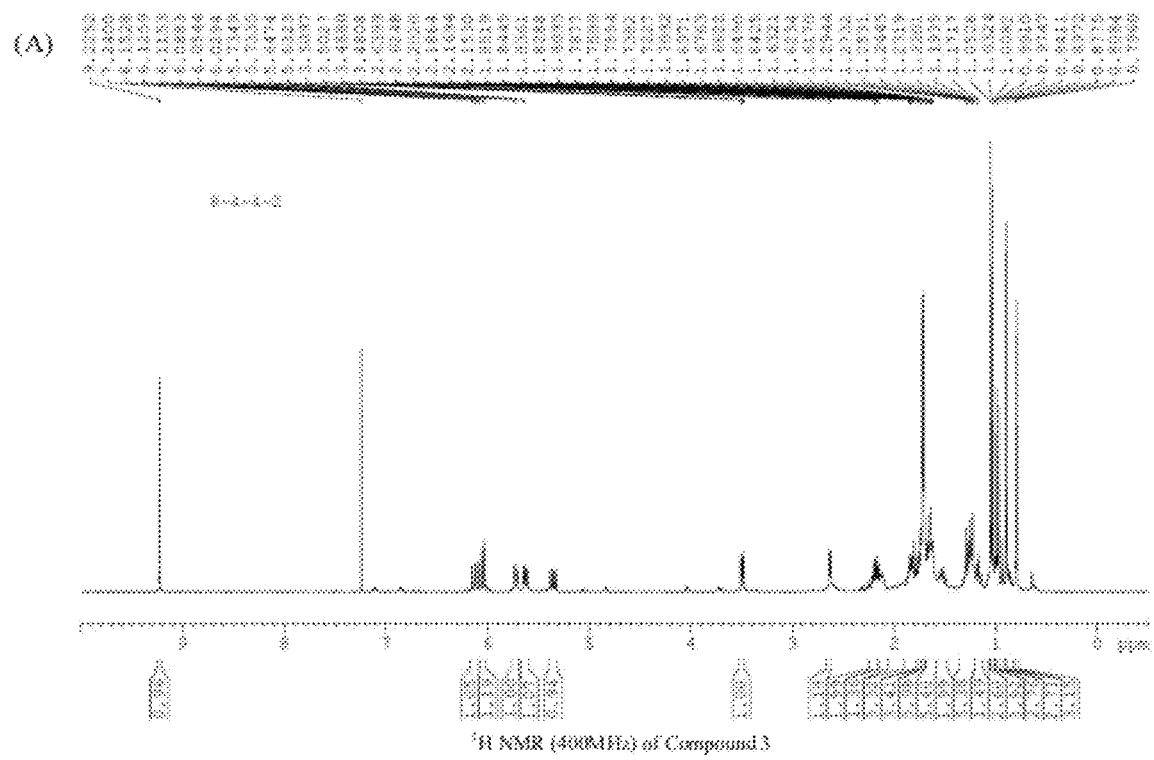
Referring to FIGS. 11A to 11E, $^1$H NMR、DEPT、EIMS、HRMS and FTIR spectrum of compound 3.
Figure 11:
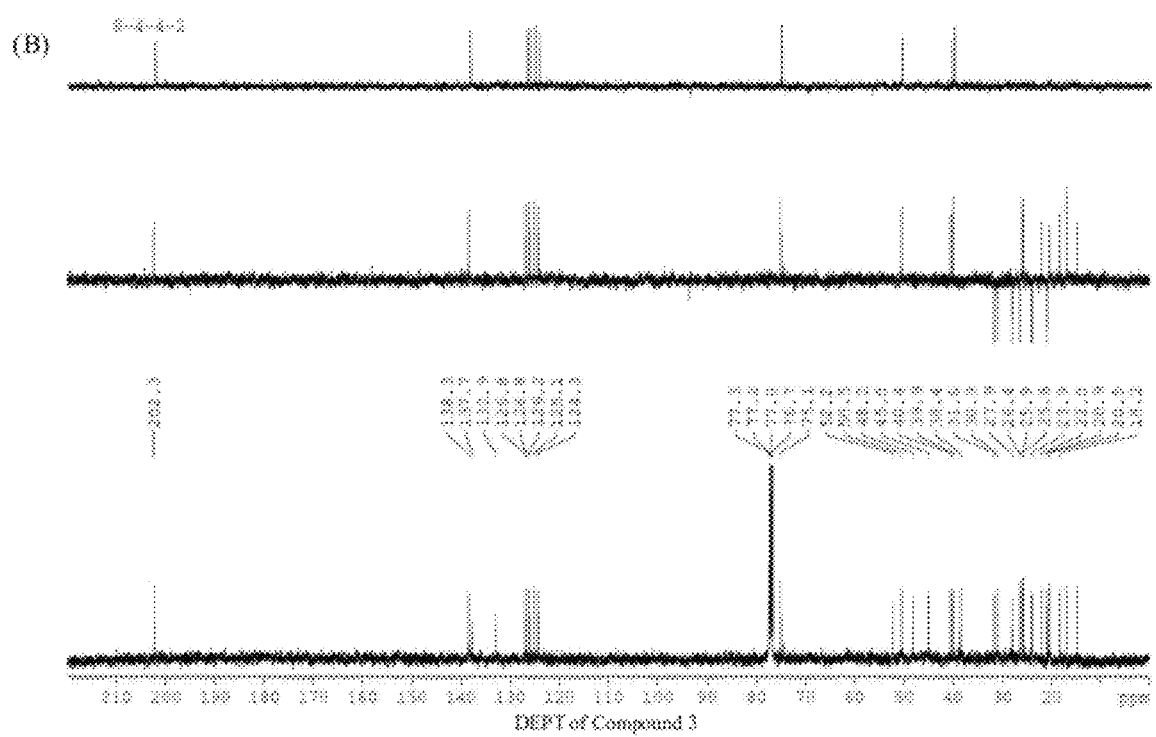
Figure 11:
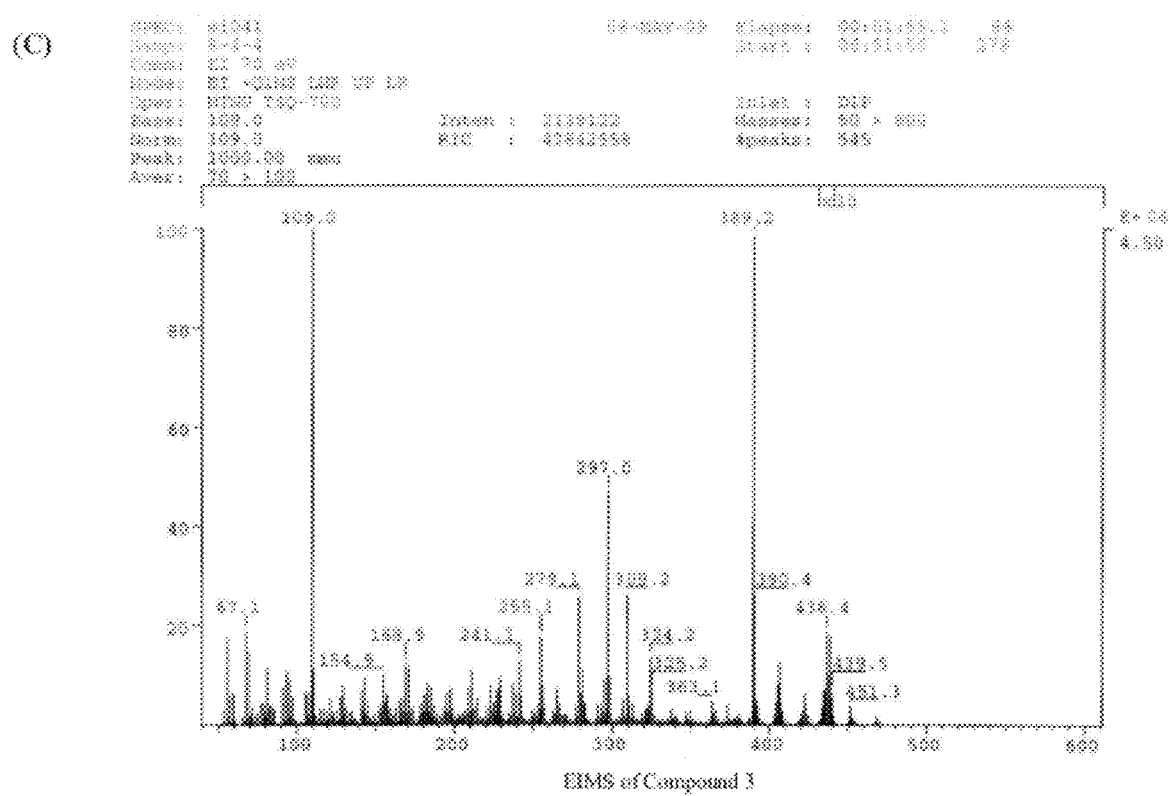
Figure 11:
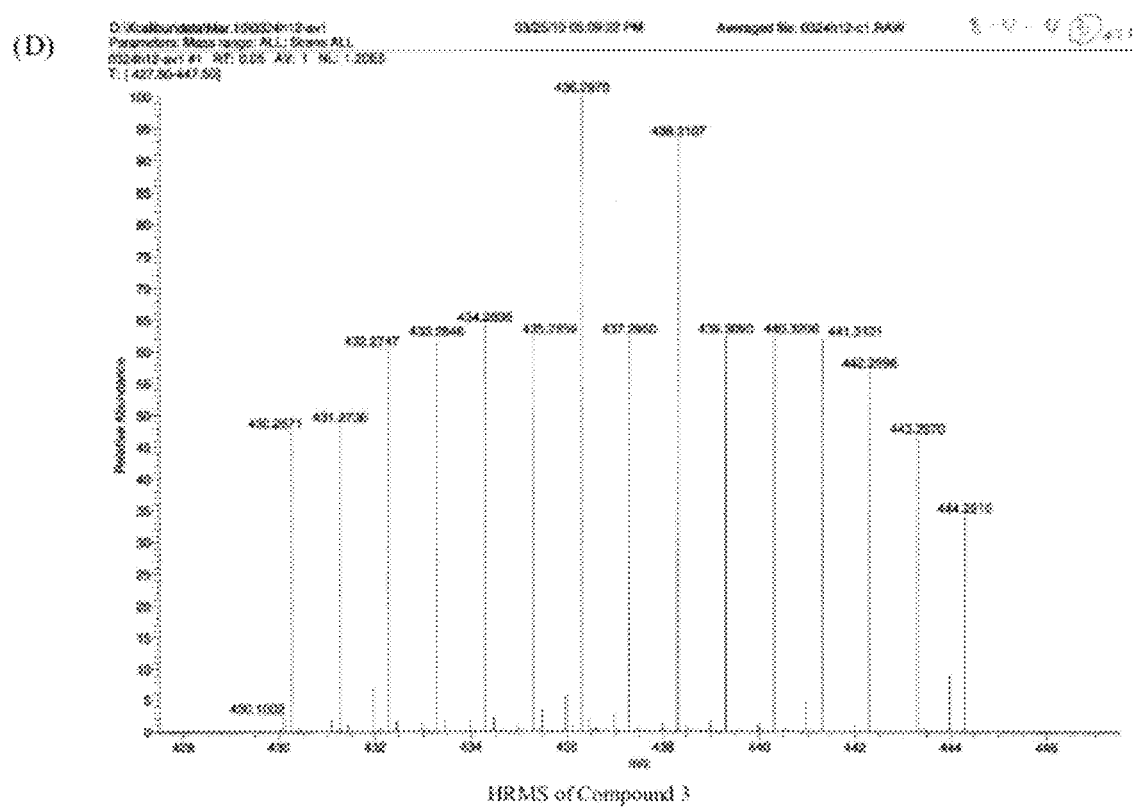
Figure 11:
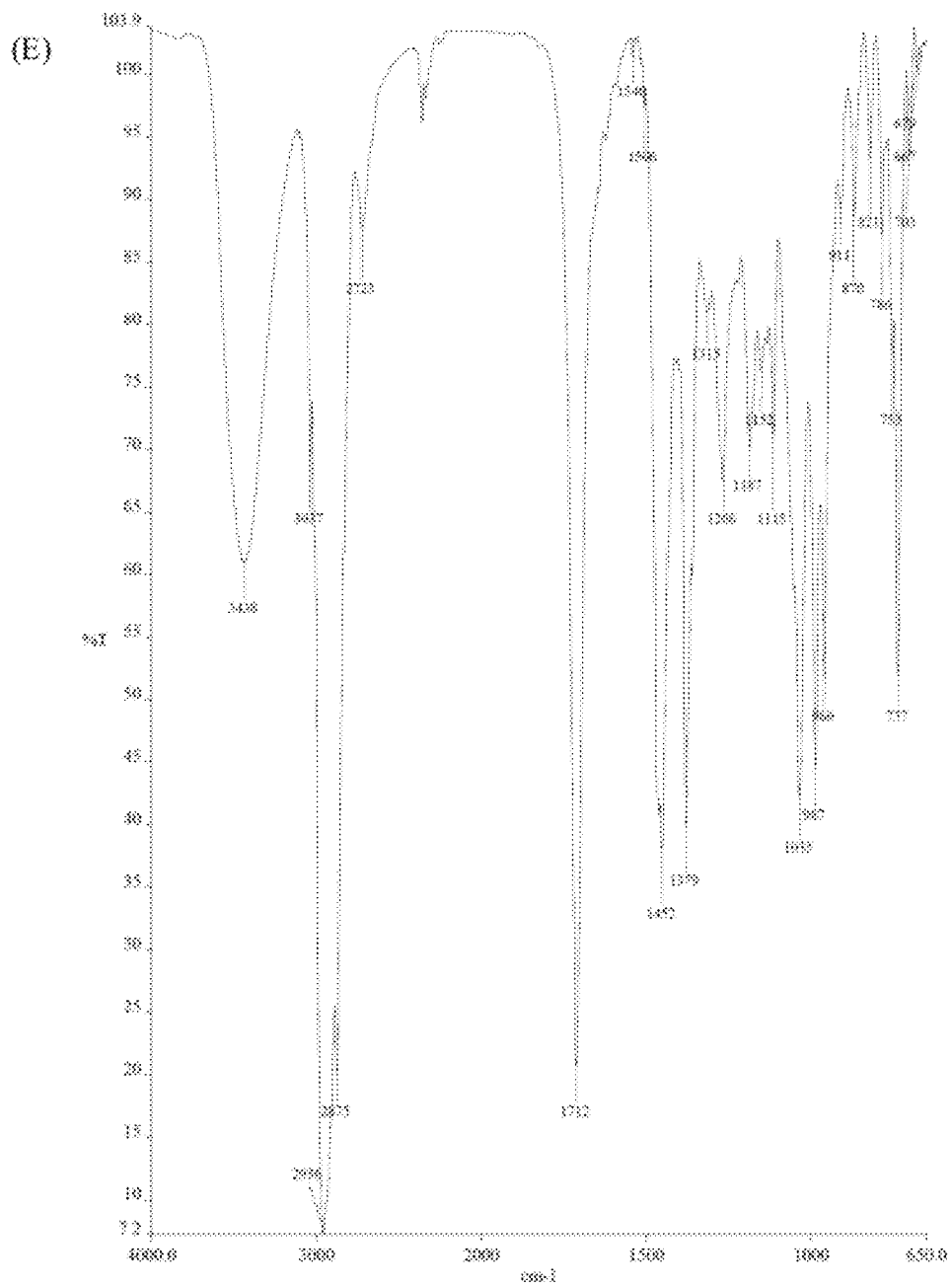
Figure 12:
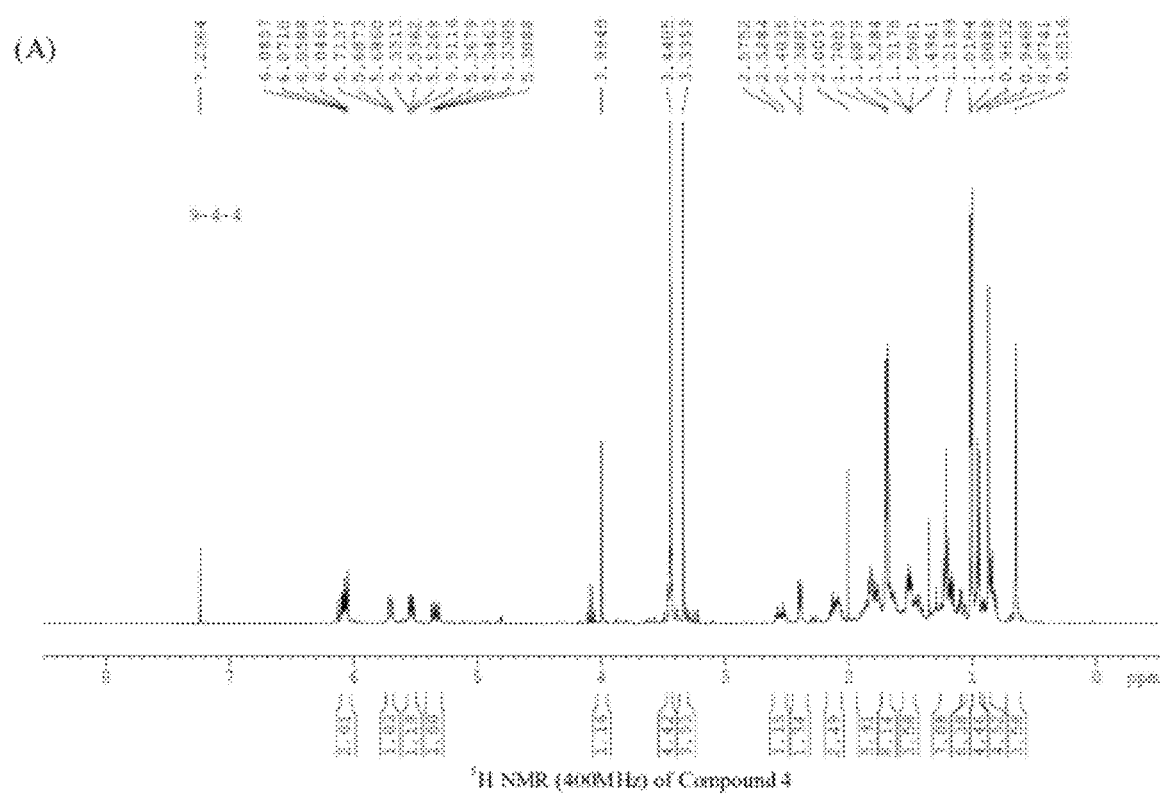
Referring to FIGS. 12A to 12E, $^1$H NMR、DEPT、EIMS、HRMS and FTIR spectrum of compound 4.
Figure 12:
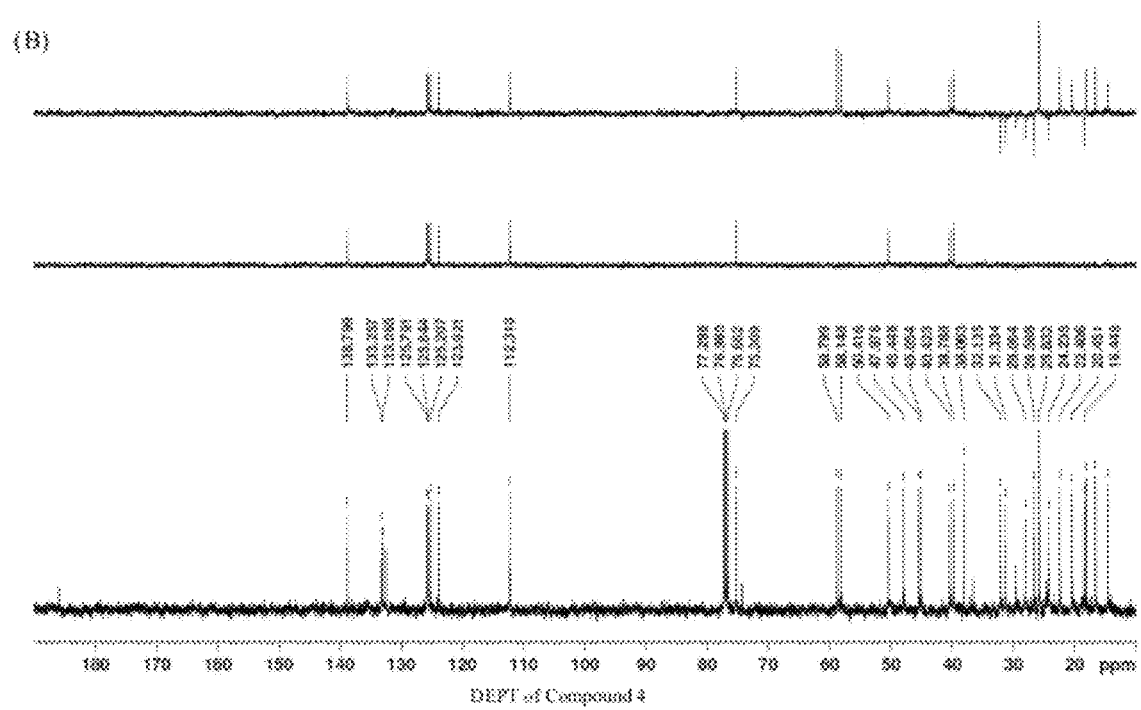
Figure 12:
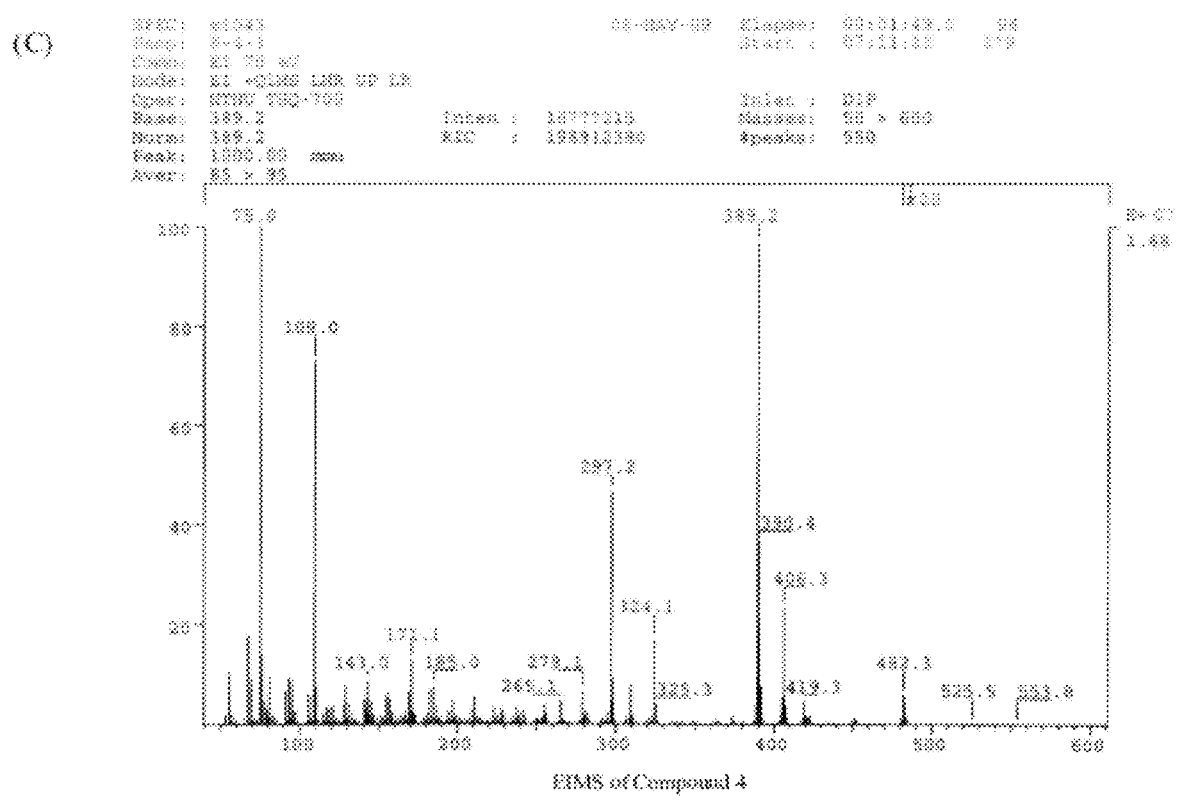
Figure 12:
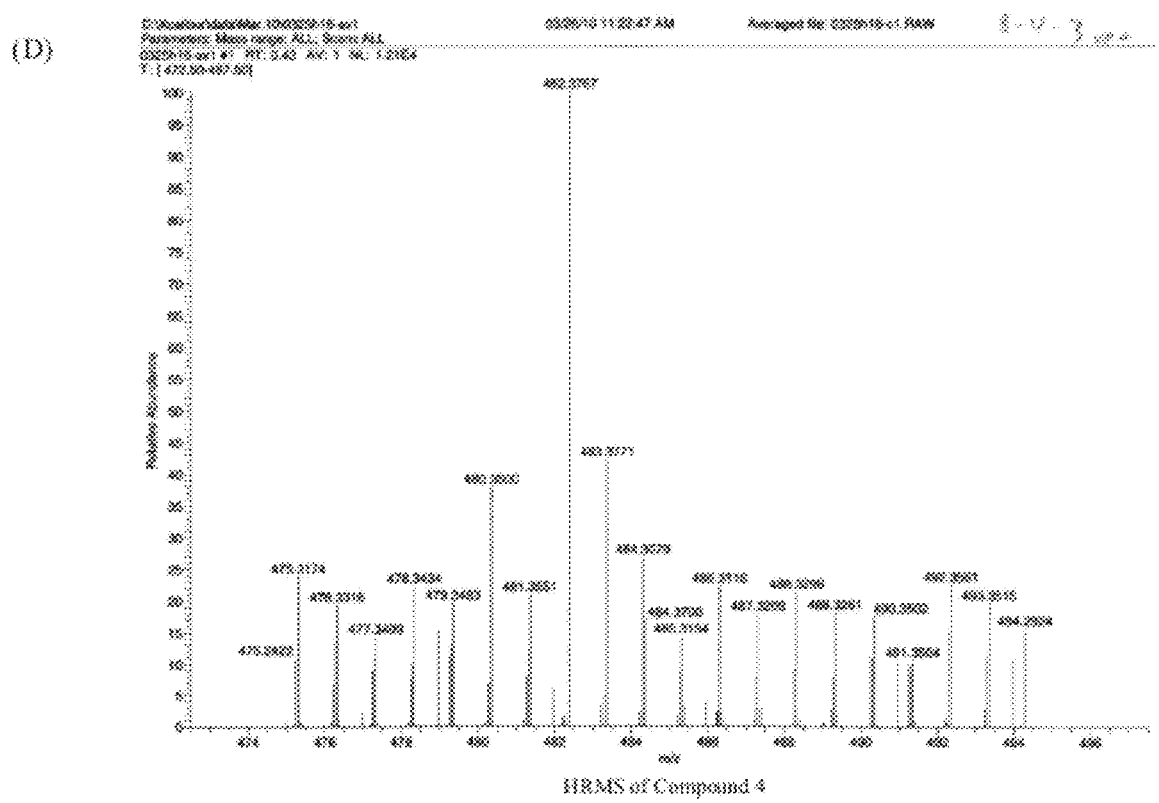
Figure 12:
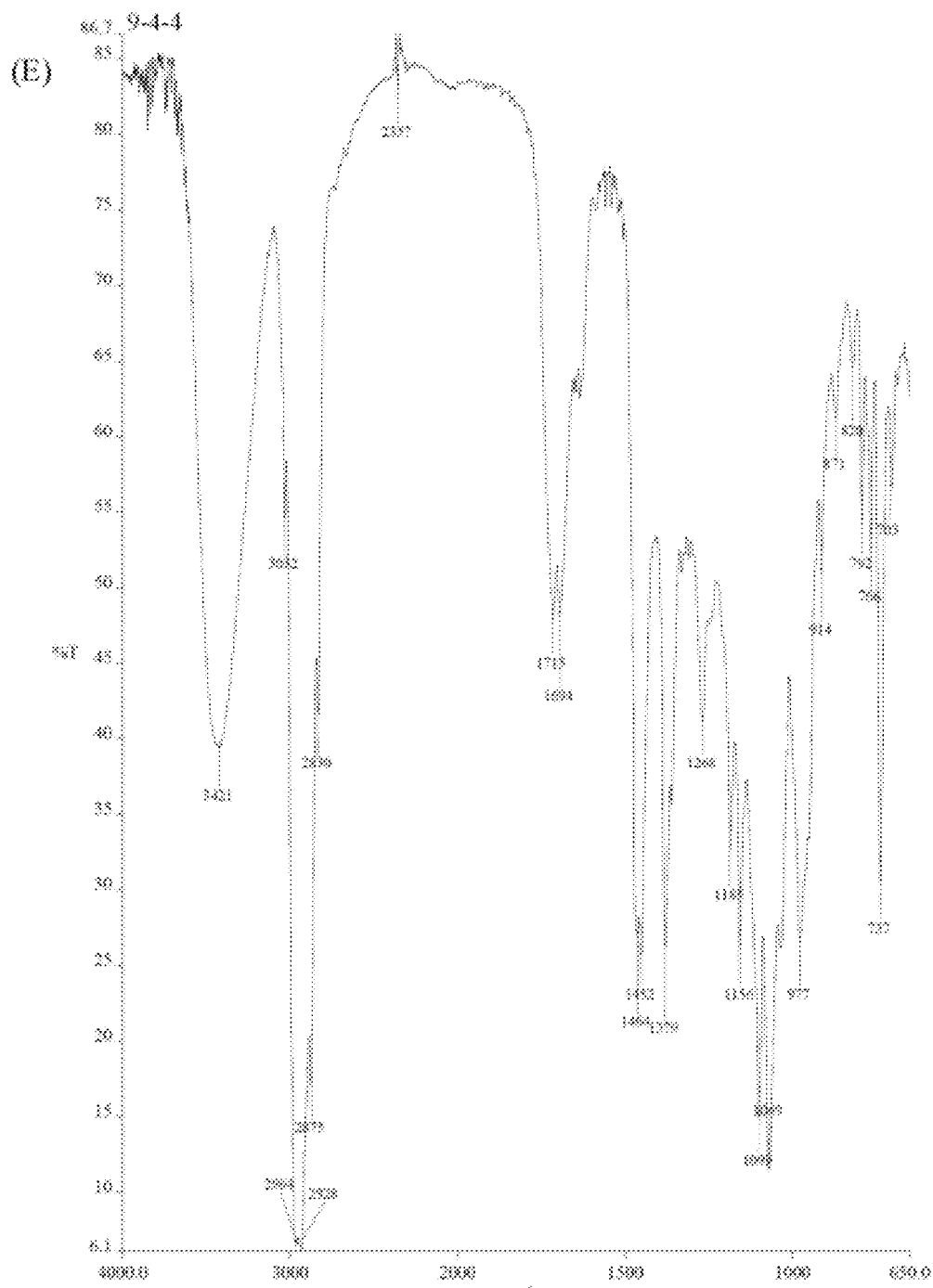
Figure 13:
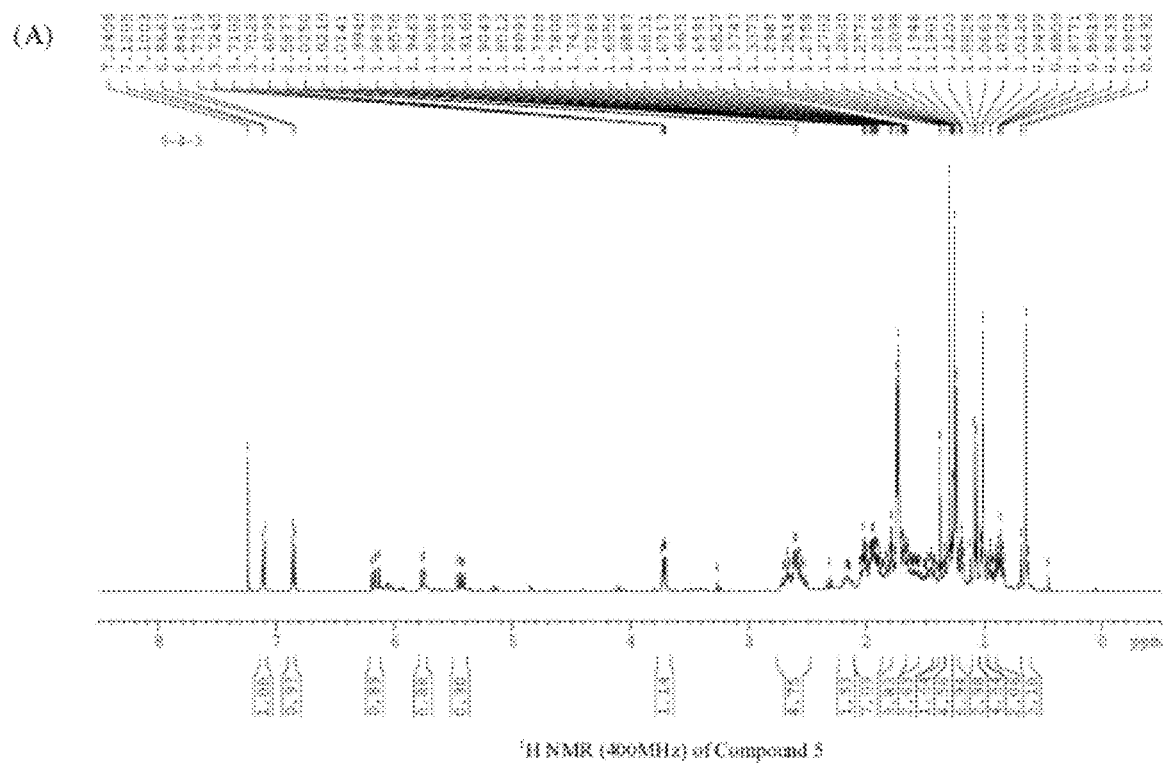
Referring to FIGS. 13A to 13E, $^1$H NMR、DEPT、EIMS、HRMS and FTIR spectrum of compound 5.
Figure 13:
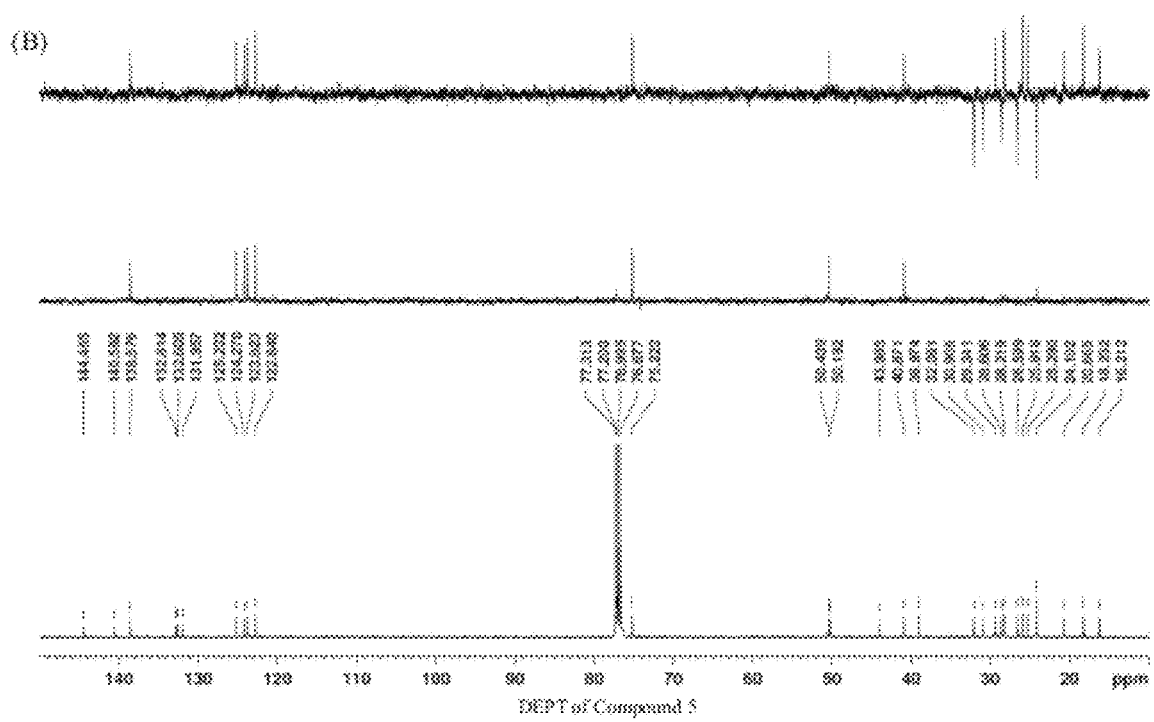
Figure 13:
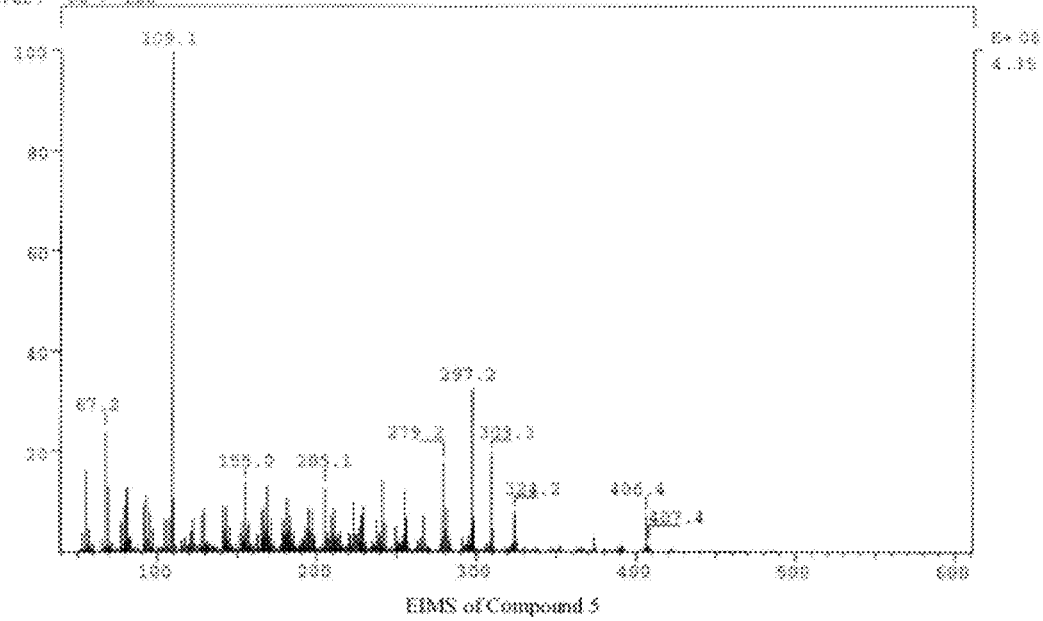
Figure 13:
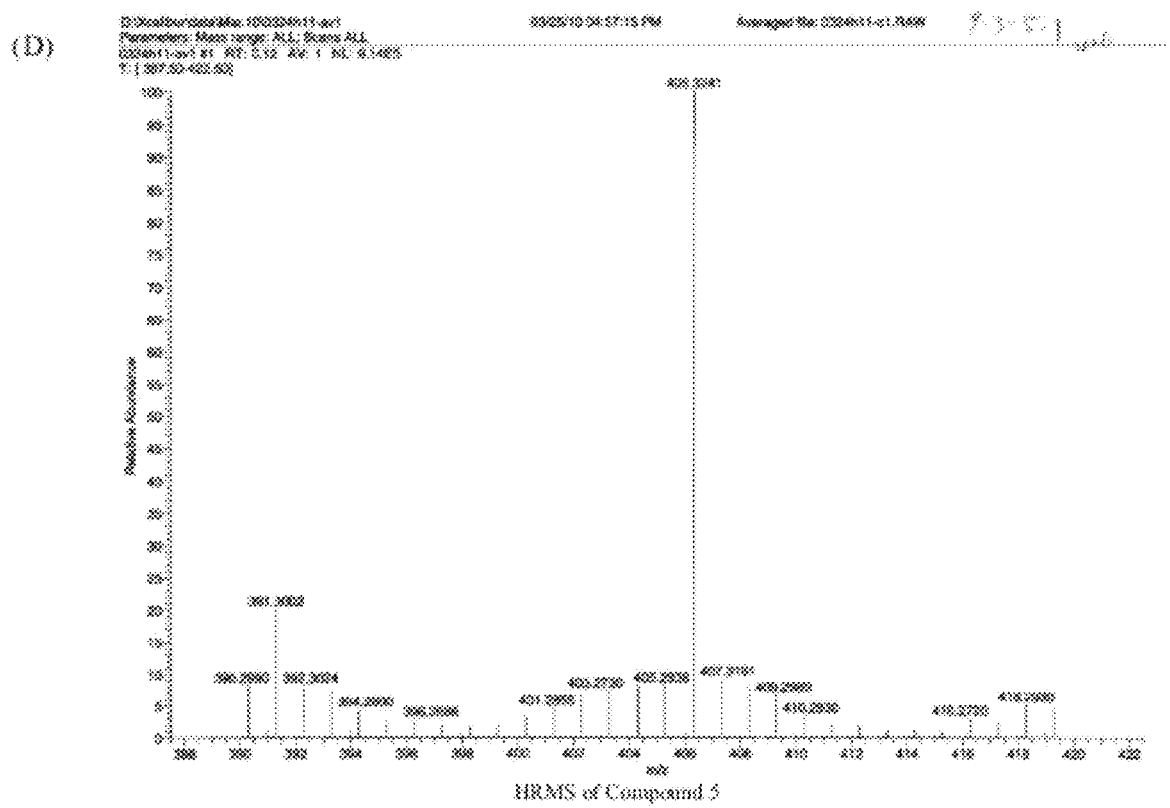
Figure 13:
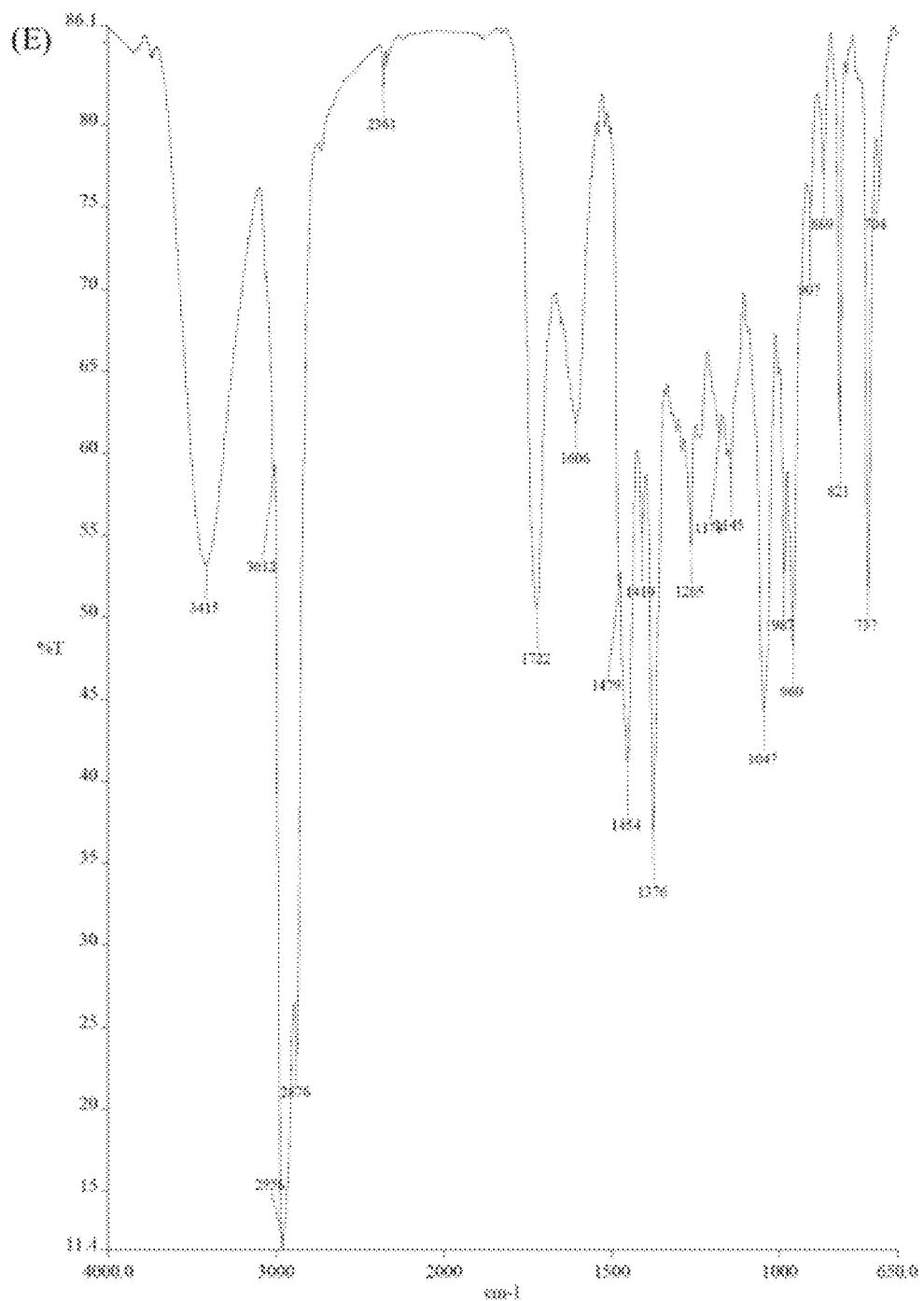

The results of FIGS. 8A and 8B was represented as means±SD from three independent experiments. * and ** labels represented significant difference after t-test ($p<0.05$ (*) and $p<0.01$ (**)) with addition of E2.

The above examples demonstrated that compound 1, 2, 5, 6, lutein and loliolide could activate ERα and ERβ. It is demonstrated that compound 1, 2, 3, 5, and 6 has antagonistic activity and can inhibited E2 induced ERα and ERβ activation when the compound and 17β-estradiol (E2) co-administered to a subject. Lutein and Loliolide with E2 has co-activation of ERα and ERβ effect.

More particularly, compounds 1-5 of the present invention can be presented in a general formula as shown in formula I:

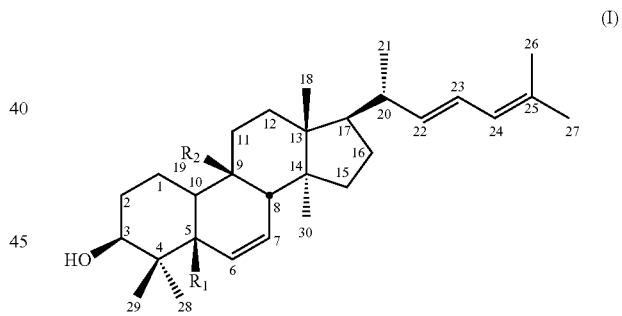

(I)

wherein a single bond or a double bond is formed between C5 and C10, and a single bond or a double bond is fromed between C8 and C9; when a single bond is formed between C5 and C10, the $R_1$ is oxygen; while a single bond is formed between C8 and C9, $R_2$ is carbonyl group (—C═O), methyl hydroxyl group (—CH(OH)), methyl ketone or methyl dimethoxy group (—CH($OCH_3$)$_2$); and wherein while $R_1$ is oxygen (—O—) and $R_2$ is carbonyl group (—C═O) or methyl hydroxyl group (—CH(OH)), a single bond is formed between $R_1$ (—O—) and C19 of $R_2$ such that $R_1$ and $R_2$ are formed tetrahydro-2H-pyran-2-one or hemiacetal ring.

The novel compounds of the present invention were cucurbita-6,22(E), 24-trien-3β-ol-19,5β-olide (compound 1), 5β,19-epoxycucurbita-6,22(E),24-trien-3β,19-diol (compound 2), 3β-hydroxycucurbita-5(10),6,22(E),24-tetraen-19-al (compound 3), 19-dimethoxycucurbita-5(10),6,22(E), 24-tetraen-3β-ol (compound 4) or 19-nor-cucurbita-5(10),6, 8,22(E),24-pentaen-3β-ol (compound 5).

Moreover, compounds 1~6 can be divided into two groups on the basis of function. The group 1 is consisted of compounds 1, 2, 5, and 6 whereas the group 2 is consisted of compounds 1, 2, 3, 5 and 6. The cucurbitane-triterpenoid compounds of the group 1 activates an estrogen receptor independently such as administering independently to activate human ERα or ERβ, or co-administered with estrogen compound (fro example, E2); and the cucurbitane-triterpenoid compounds of the group 2 partly activates ER activity induced by endogenous estrogen. Biological functions of these compounds have not been disclosed, and their applications for regulation of estrogen receptors are novel.

Furthermore, the cucurbitane-triterpenoid compounds can be applied as a pharmaceutical composition for regulation of estrogen receptor activity, which comprises Group 1 or Group 2, combinations or pharmaceutically acceptable salts thereof; and a diluent, an excipient or a carrier.

The active ingredients described above, no matter in simple compound or a pharmaceutical composition can be applied in women suffering menopause symptoms or estrogen deficiency patients. For example, the cucurbitane-triterpenoid compounds of Group 1 can activate estrogen receptor to treat or improve symptoms, and can be co-administered with estrogen drugs to selectively activate estrogen receptor. Thus these compounds have great potential to be developed as therapeutics or dietary supplements to relieve women with menopause symptoms or patients with estrogen deficiency diseases. The cucurbitane-triterpenoid compounds of Group 2 can partly inhibit ER activity induced by endogenous estrogen. For example, these compounds can inhibit endogenous estrogen activation and alleviate cancer proliferation in estrogen dependent breast cancer patients.

The present invention is explained in the above embodiment illustration and examples. Those examples above should not, however, be considered to limit the scope of the invention, it is contemplated that modifications will readily occur to those skilled in the art, which modifications will be within the spirit of the invention and the scope of the appended claims.

What is claimed is:

1. A cucurbitane-triterpenoid compound represented by the following formula (I):

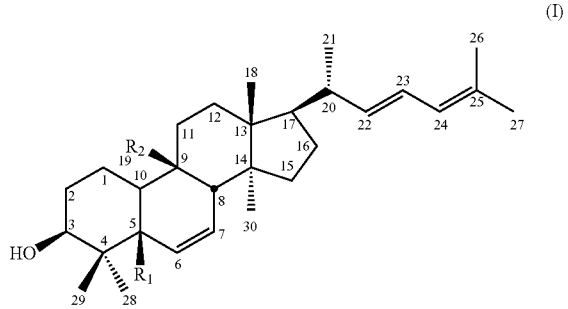

(I)

wherein a single bond or a double bond is formed between C5 and C10, and a single bond or a double bond is fromed between C8 and C9; when a single bond is formed between C5 and C10, the $R_1$ is oxygen; while a single bond is formed between C8 and C9, $R_2$ is carbonyl group (—C=O), methyl hydroxyl group (—CH(OH)), methyl ketone or methyl dimethoxy group (—CH(OCH$_3$)$_2$); and wherein while $R_1$ is oxygen (—O—) and $R_2$ is carbonyl group (—C=O) or methyl hydroxyl group (—CH(OH)), a single bond is formed between $R_1$ (—O—) and C19 of $R_2$ such that $R_1$ and $R_2$ are formed tetrahydro-2H-pyran-2-one or hemiacetal ring.

2. The compound of claim 1, wherein the compound is cucurbita-6,22(E), 24-trine-3β-ol-19,5β-olide (compound 1), 5β,19-epoxycucurbita-6,22(E),24-trien-3β,19-diol (compound 2), 3β-hydroxycucurbita-5(10),6,22(E),24tetraen-19-al (compound 3), 19-dimethoxycucurbita-5(10),6,22(E),24-tetraen-3β-ol (compound 4) or 19-nor-cucurbita-5(10),6,8,22(E),24-pentaen-3β-ol (compound 5).

3. An estrogen receptor regulator, comprising a group 1 or a group 2, wherein the group 1 is consisted of cucurbita-6,22 (E),24-trien-3β-ol-19,5β-olide (compound 1), 5β,19-epoxycucurbita-6,22(E),24-trien-3β,19-diol (compound 2), and 19-nor-cucurbita-5(10),6,8,22(E),24-pentaen-3β-ol (compound 5); and the group 2 is consisted of cucurbita-6,22(E),24-trien-3β-ol-19,5β-olide (compound 1), 5β,19-epoxycucurbita-6,22(E),24-trien-3β,19-diol (compound 2), 3β-hydroxycucurbita-5(10),6,22(E),24-tetraen-19-al (compound 3), 19-nor-cucurbita-5(10),6,8,22(E),24-pentaen-3β-ol (compound 5), combinations or pharmaceutically acceptable salts thereof; and a diluent, an excipient or a carrier.

4. A method for preparing the cucurbitane-triterpenoid compound of formula I as defined by claim 1 from *Momordica charantia*, comprising steps of:
(a) extracting a pre-determined weight of *Momordica charantia* freeze dry powder with ethyl acetate at room temperature, evaporating by reduced pressure to remove ethyl acetate and obtaining an ethyl acetate extract and a residue;
(b) extracting the residue with ethanol at room temperature, evaporating by reduced pressure to remove ethanol and obtaining an ethanol extract;
(c) separating the ethanol extract with reverse phase column chromatography having coarse particle to obtain fraction 1, acid hydrolyzing the fraction 1 and extracting with ethyl acetate at room temperature, evaporating by reduced pressure to remove solvents and obtaining an acid hydrolysate;
(d) separating the acid hydrolysate with reverse phase column chromatography to obtain fraction 2; and
(e) purifying the fraction 2 of step (d) by using reverse phase and normal phase preparative HPLC to obtain the cucurbitane-triterpenoid compound with estrogenic activity.

5. The method of claim 4, wherein the *Momordica charantia* freeze dry powder is extracted with twenty volumes of ethyl acetate in the step (a).

6. The method of claim 4, wherein the residue is extracted with twenty volumes of ethanol in the step (b).

7. The method of claim 4, wherein the ethanol extract is eluted by reverse phase column in the order with water, 50% methanol/water, 100% methanol and acetone as mobile phase in the step (c).

8. The method of claim 4, wherein the ethanol extract is eluted with 80% methanol/water, followed by water, 50% methanol/water, 100% methanol and acetone to obtain and acid hydrolyze the fraction 1 in the step (c).

9. The method of claim 4, wherein the fraction 1 is acid hydrolyzed with hydrogen chloride in the step (c).

10. The method of claim 4, wherein the acid hydrolysate is eluted by reverse phase column in order with 80% methanol/water and 100% methanol as mobile phase in the step (d).

11. The method of claim 4, wherein the fraction 2 is either eluted by the reverse phase preparative HPLC with 100% methanol or 100% methanol with 0.1% acetic acid as mobile phase, or the fraction 2 is eluted by normal phase HPLC with ethyl acetate/n-hexane with ratio of 3:7 or THF/n-hexane with ratio of 2:8 in the step (e).

* * * * *